(12) United States Patent
Raisoni et al.

(10) Patent No.: US 10,945,644 B2
(45) Date of Patent: Mar. 16, 2021

(54) REMOTE ANALYTE MONITORING

(71) Applicant: Senseonics, Incorporated, Germantown, MD (US)

(72) Inventors: Barkha Raisoni, Germantown, MD (US); Barbara Montgomery, Gaithersburg, MD (US); Andrew Dehennis, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 112 days.

(21) Appl. No.: 15/896,600

(22) Filed: Feb. 14, 2018

(65) Prior Publication Data

US 2018/0228408 A1 Aug. 16, 2018

Related U.S. Application Data

(60) Provisional application No. 62/458,836, filed on Feb. 14, 2017.

(51) Int. Cl.
| | |
|---|---|
| *A61B 5/1455* | (2006.01) |
| *A61B 5/145* | (2006.01) |
| *A61B 5/00* | (2006.01) |
| *G16H 50/20* | (2018.01) |
| *G16H 40/60* | (2018.01) |
| *G16H 50/30* | (2018.01) |
| *G16H 80/00* | (2018.01) |
| *G16H 40/67* | (2018.01) |

(52) U.S. Cl.
CPC ............ *A61B 5/145* (2013.01); *A61B 5/0022* (2013.01); *A61B 5/14532* (2013.01); *A61B 5/7435* (2013.01); *A61B 5/7445* (2013.01); *G16H 40/60* (2018.01); *G16H 40/67* (2018.01); *G16H 50/20* (2018.01); *G16H 50/30* (2018.01); *G16H 80/00* (2018.01)

(58) Field of Classification Search
None
See application file for complete search history.

(56) References Cited

U.S. PATENT DOCUMENTS

| | | | |
|---|---|---|---|
| 8,073,548 B2 | 12/2011 | Colvin, Jr. et al. | |
| 9,414,775 B2 | 8/2016 | Colvin, Jr. et al. | |
| 9,514,277 B2 | 12/2016 | Hassing et al. | |
| 9,693,714 B2 | 7/2017 | DeHennis et al. | |

(Continued)

*Primary Examiner* — Marjan Fardanesh
(74) *Attorney, Agent, or Firm* — Rothwell, Figg, Ernst & Manbeck, P.C.

(57) ABSTRACT

An analyte monitoring system may include one or more sensors, one or more transceivers, one or more primary display devices, a remote computing device, and one or more secondary display devices. Each sensor may be in communication with a respective transceiver, and each transceiver may be in communication with a respective primary display device. A patient application may be stored as computer readable instructions in a storage medium of a primary display device, and an observer application is stored as computer readable instructions in a storage medium of a secondary display device. The patient application may be configured to allow a user of the primary display device to share analyte information with a secondary display device. The observer application may be configured to allow a user of the secondary display device to receive and display the shared analyte information.

16 Claims, 22 Drawing Sheets

(56) References Cited

U.S. PATENT DOCUMENTS

| | | |
|---|---|---|
| 9,801,541 B2 | 10/2017 | Mensinger et al. |
| 9,839,353 B2 | 12/2017 | Mensinger et al. |
| 9,854,972 B2 | 1/2018 | Mensinger et al. |
| 9,962,081 B2 | 5/2018 | Mensinger et al. |
| 9,980,646 B2 | 5/2018 | Mensinger et al. |
| 2013/0117696 A1* | 5/2013 | Robertson ........... G06F 19/3456 715/763 |
| 2013/0241745 A1 | 9/2013 | Colvin, Jr. et al. |
| 2014/0187889 A1 | 7/2014 | Cohen et al. |
| 2015/0182115 A1 | 7/2015 | DeHennis |
| 2016/0066866 A1 | 3/2016 | Mensinger et al. |
| 2016/0270740 A1 | 9/2016 | Raisoni et al. |
| 2016/0345830 A1 | 12/2016 | Raisoni et al. |

* cited by examiner

FIG. 12A

REMOTE ANALYTE MONITORING

CROSS-REFERENCE TO RELATED APPLICATION

The present application claims the benefit of priority to U.S. Provisional Application Ser. No. 62/458,836, filed on Feb. 14, 2017, which is incorporated herein by reference in its entirety.

BACKGROUND

Field of the Invention

This disclosure relates to an analyte monitoring system for sharing a patient's analyte information with one or more persons.

Discussion of the Background

Analyte monitoring systems may be used to monitor analyte levels, such as analyte concentrations. One type of analyte monitoring system is a continuous glucose monitoring (CGM) system. A CGM system measures glucose levels throughout the day and can be very useful in the management of diabetes. Although analyte monitoring systems enable patients to monitor their analyte levels, they do not allow others to monitor the analyte levels of the patients.

SUMMARY

The present invention overcomes the disadvantages of prior systems by providing, among other advantages, an improved analyte monitoring system that enables one or more persons to monitor analyte levels in one or more patients.

One aspect of the invention may provide an analyte monitoring system including a analyte sensor, a transceiver, a primary display device, a remote computing device, and a secondary display devices. The analyte sensor may include an indicator element that exhibits one or more detectable properties based on an amount or concentration of an analyte in proximity to the indicator element. The analyte sensor may be configured to convey sensor data. The transceiver may be configured to receive the sensor data conveyed from the analyte sensor, calculate analyte information using at least the received sensor data, and convey the analyte information. The primary display device may be configured to receive the analyte information conveyed from the transceiver, display the received analyte information, and convey the analyte information over a network. The remote computing device may be configured to receive the analyte information conveyed from the primary display device over the network. The secondary display device may be configured to receive the analyte information from the remote computing device over the network and to display the received analyte information.

In some embodiments, the remote computing device may include a server. In some embodiments, the analyte sensor may be a first analyte sensor, the indicator element may be a first indicator element, the sensor data may be first sensor data, the transceiver may be a first transceiver, the analyte information may be first analyte information, and the primary display device may be a first primary display device. The analyte monitoring system may further include a second analyte sensor, a second transceiver, and a second primary display device. The second analyte sensor may include a second indicator element that exhibits one or more detectable properties based on an amount or concentration of the analyte in proximity to the second indicator element. The second analyte sensor may be configured to convey second sensor data. The second transceiver may be configured to receive the second sensor data conveyed from the second analyte sensor, calculate second analyte information using at least the received second sensor data, and convey the second analyte information. The second primary display device may be configured to receive the second analyte information conveyed from the second transceiver, display the received second analyte information, and convey the second analyte information over the network. The remote computing device may be configured to receive the second analyte information conveyed from the second primary display device over the network. The secondary display device may be configured to receive the second analyte information from the remote computing device over the network and to display the received second analyte information.

In some embodiments, the primary display device may include a storage medium and a processor. In some embodiments, the storage medium may store a patient application in the form of computer readable instructions. In some embodiments, the processor may be configured to execute one or more of the computer readable instructions of the patient application. In some embodiments, the patient application may be configured to allow a user of the primary display device to share analyte information with the secondary display device.

In some embodiments, the secondary display device may include a storage medium and a processor. In some embodiments, the storage medium may store an observer application in the form of computer readable instructions. The processor may be configured to execute one or more of the computer readable instructions of the observer application. The observer application may be configured to allow a user of the secondary display device to receive and view analyte information from the primary display device. In some embodiments, an observer operating the secondary display device may follow and keep track of the analyte information of the patient in real time.

One aspect of the present invention may provide a method for sharing analyte information associated with a host to one or more remote users. The method may comprise the step of conveying, by an analyte sensor, sensor data to a transceiver. The method may comprise the step of calculating, by the transceiver, analyte information using at least the received sensor data. The method may comprise the step of conveying, by the transceiver, the analyte information to a primary display device. The method may comprise the step of conveying, by the primary display device, the analyte information over a network to a remote computing device configured to store the analyte information. The method may comprise the step of transmitting, by the primary display device, an invitation authorizing access to the analyte information stored in the remote computing device over a network to one or more secondary display devices, wherein each secondary display device is configured to be used by a respective user who is remote to the analyte sensor.

In some embodiments, the analyte information comprises one or more of: (i) an analyte concentration, (ii) an alert, (iii) an alarm, and (iv) analyte concentration trend information. In some embodiments, the analyte information comprises one or more of a high analyte alarm level, a low analyte alarm level, a high target analyte level, and a low target analyte level. In some embodiments, the analyte sensor comprises an indicator element that exhibits one or more detectable properties based on an amount or concentration of an analyte in proximity to the indicator element, and the sensor data corresponds to the amount or concentration of the analyte in proximity to the indicator element. In some embodiments, the transceiver comprises a sensor interface device configured to convey a power signal to the analyte sensor and to receive data signals conveyed by the analyte sensor.

One aspect of the present invention may provide a method for receiving and monitoring analyte information at a secondary display device. The method may comprise the step of receiving, at a secondary display device, an invitation transmitted from a primary display device, wherein the invitation authorizes the secondary display device to access analyte information, and the secondary display device is remote from the primary display device. The method may comprise the step of accepting, by the secondary display device, the invitation by downloading an observer application into a memory of the secondary display device. The method may comprise the step of receiving, by the secondary display device, the analyte information. The method may comprise the step of generating, by executing the observer application on the secondary display device, one or more alarms, alerts, or notifications based on the received analyte information. In some embodiments, the analyte information associated with each host comprises one or more of: (i) an analyte concentration (ii) an alert, (iii) an alarm, and (iv) analyte concentration trend information.

In some embodiments, the method may include the step of displaying, by executing the observer application on the secondary display device, a host status bar that identifies a host associated with the primary display device and indicates a status of the host using at least a portion of the received analyte information. In some embodiments, the method may include the step of selecting, by user input to the secondary display device, one of a plurality of host status bars. In some embodiments, the method may include the step of displaying, by the secondary device, an analyte trend graph associated with the selected host status bar, wherein the analyte trend graph comprises a trend line indicating a plurality of analyte concentrations over a first time interval.

In some embodiments, the method may include the step of selecting, by user input to the secondary display device, the displayed analyte trend graph that is associated with the selected host status bar. In some embodiments, the method may include the step of displaying, by the secondary display device, a list of alarms, alerts, and/or notifications generated by the observer application over a period of time and a selectable icon corresponding to each alarm, alert, or notification. In some embodiments, each selectable icon indicates one more of a type, a severity, and a frequency of the respective alarm, alert, or notification.

In some embodiments, the method may include the step of selecting, by user input to the secondary display device, the list of alarms, alerts, and/or notifications associated with a selected one of a plurality of hosts. In some embodiments, the method may include the step of displaying, by the secondary display device, an event log depicting a plurality of events associated with the selected host and a selectable icon corresponding to each of the events. In some embodiments, the selectable icon corresponding to each of the plurality of events comprises one or more of: a blood glucose meter test icon, a meal event icon, an insulin dosage icon, a health condition icon, and an exercise event icon.

In some embodiments, the method may include the step of displaying, by executing the observer application on the secondary display device, a number of host status bars. In some embodiments, the method may include the step of determining, by executing the observer application on the secondary display device, that the number of host status bars displayed on the secondary display device is equal to a maximum number of hosts. In some embodiments, the method may include the step of displaying, by executing the observer application on the secondary display device, a message indicating that a number of accepted invitations has met the maximum number of hosts.

One aspect of the present invention may provide an analyte monitoring system. The analyte monitoring system may comprise an analyte sensor including an indicator element that exhibits one or more detectable properties based on an amount or concentration of an analyte in proximity to the indicator element, wherein the analyte sensor is configured to convey sensor data. The analyte monitoring system may comprise a primary display device configured to: (i) receive the sensor data conveyed from the analyte sensor, (ii) calculate analyte information using at least the received sensor data, (iii) display the received analyte information, and (iv) convey the analyte information over a network. The analyte monitoring system may comprise a remote computing device configured to receive the analyte information conveyed from the primary display device over the network. The analyte monitoring system may comprise a secondary display device configured to: (i) receive the analyte information form the remote computing device over the network and (ii) display the received analyte information.

One aspect of the present invention may provide a method for generating and authorizing analyte information. The method may comprise the step of conveying, by an analyte sensor, sensor data to a primary display device. The method may comprise the step of calculating, by the primary display device, analyte information using at least the received sensor data. The method may comprise the step of conveying, by the primary display device, the analyte information over a network to a remote computing device configured to store the analyte information. The method may comprise the step of transmitting, by the primary display device, an invitation authorizing access to the analyte information stored in the remote computing device over a network to one or more secondary display devices, wherein each secondary display device is configured to be used by a respective user who is remote to the analyte sensor.

One aspect of the present invention may provide a non-transitory tangible computer readable medium comprising computer readable instruction to be executed by one or more processors in a secondary display device. The instruction of the medium may cause the secondary display device to receive one or more invitations transmitted from one or more primary display devices configured to be used by one or more hosts, wherein each primary display device is associated with a respective host, and each invitation authorizes the secondary display device to access analyte information associated with the respective host. The instruction of the medium may cause the secondary display device to generate a notification requesting the user to authorize the secondary display device to generate alerts, notifications, and alarms based on the analyte information associated with the one or more hosts. The instruction of the medium may cause the secondary display device to receive the analyte information associated with the one or more hosts in response to the user authorizing the secondary display device to generate alerts, notifications, and alarms. The instruction of the medium may cause the secondary display device to generate one or more alarms, alerts, and notifications based on the received analyte information associated with the one or more hosts. In some embodiments, the analyte information associated with each host comprises one or more of: (i) an analyte concentration associated with a time stamp, (ii) alerts, (iii) alarms, and (iv) analyte concentration trend information, and each analyte information is derived from sensor data obtained by an analyte sensor associated with the respective host.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIGS. 12A, 12B, 12C, 12D, and 12E show various example home screens embodying aspects of the present invention.

DETAILED DESCRIPTION

The Analyte Monitoring System

Figure 1:
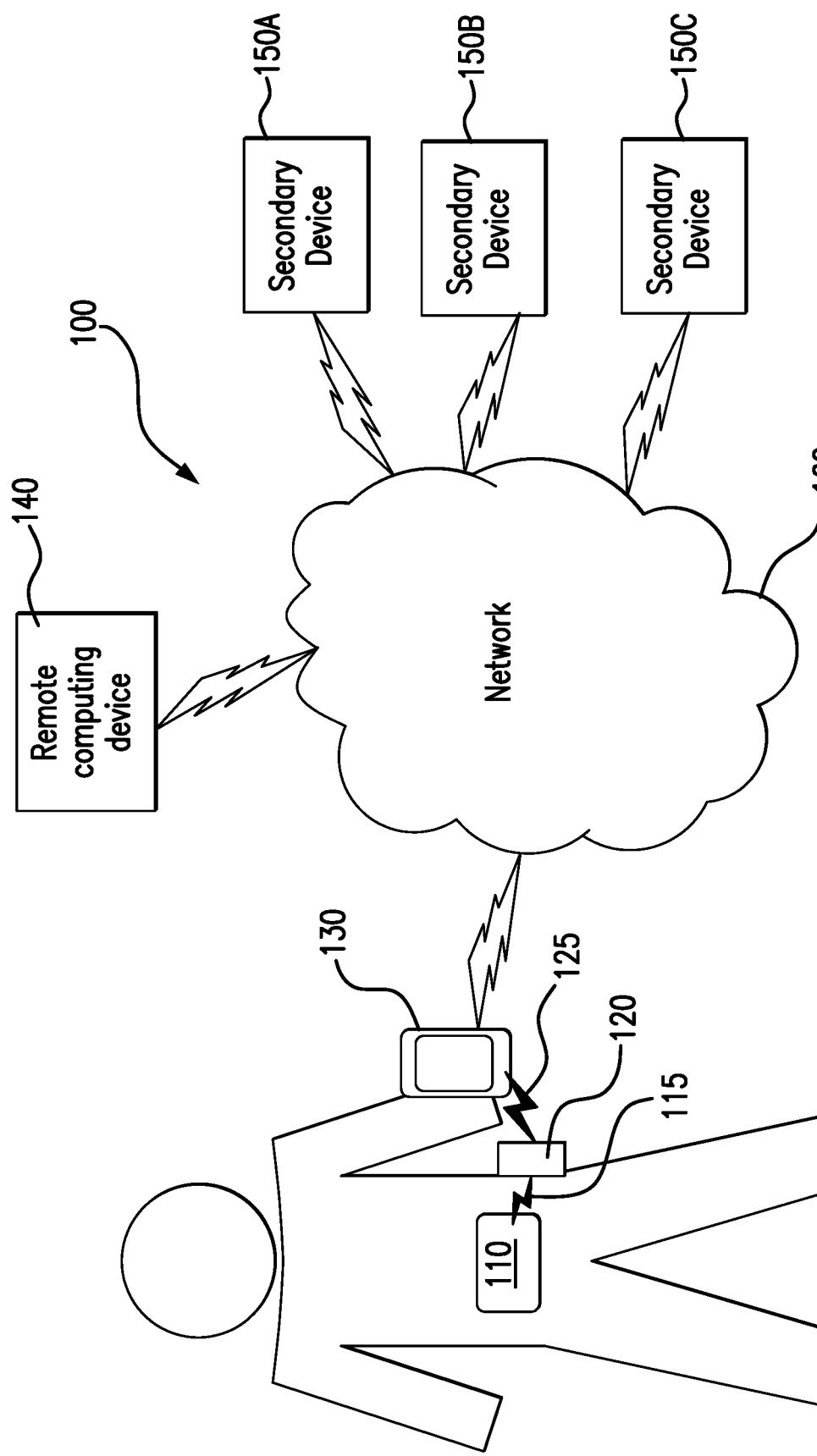
FIG. 1 is a schematic view illustrating an analyte monitoring system embodying aspects of the present invention.

FIG. 1 is a schematic view of an analyte monitoring system 100 embodying aspects of the present invention. The analyte monitoring system 100 may be a continuous analyte monitoring system (e.g., a continuous glucose monitoring system). In some embodiments, as shown in FIG. 1, the analyte monitoring system 100 may include one or more of an analyte sensor 110, a transceiver 120, a primary display device 130, a remote computing device 140, and one or more secondary display devices 150A-C. In some embodiments, the analyte sensor 110 may be in communication with the transceiver 120 over a first communication link 115. The first communication link 115 may be a wireless communication link or a wired communication link. Examples of wired communication links comprise, but are not limited to: cable, wire, twisted-pair wire, fiber-optic, Ethernet, USB, and/or the like. Examples of wireless communications links comprise, but are not limited to: cellular, Wi-Fi, Bluetooth™, Near-Field Communications (NFC), infrared, radar, satellite, radio frequency, combinations thereof, and/or the like. In some embodiments, the transceiver 120 may be in communication with the primary display device 130 by a second communication link 125. Each of the first and second communication links 115 and 125 may be a wireless communication link or a wired communication link. Examples of wired communication links comprise, but are not limited to: cable, wire, twisted-pair wire, fiber-optic, Ethernet, USB, and/or the like. Examples of wireless communications links comprise, but are not limited to: cellular, Wi-Fi, Bluetooth™, Near-Field Communications (NFC), infrared, radar, satellite, radio frequency, combinations thereof, and/or the like.

In some embodiments, the sensor 110 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 110 may be a partially implantable (e.g., transcutaneous) sensor or a fully external sensor. In some embodiments, the transceiver 120 may be an externally worn transceiver (e.g., attached via an armband, wristband, waistband, or adhesive patch). In some embodiments, the transceiver 120 may remotely power and/or communicate with the sensor to initiate and receive the measurements (e.g., via near field communication (NFC)). However, this is not required, and, in some alternative embodiments, the transceiver 120 may power and/or communicate with the sensor 110 via one or more wired connections. In some non-limiting embodiments, the transceiver 120 may be a smartphone (e.g., an NFC-enabled smartphone). In some embodiments, the transceiver 120 may communicate information (e.g., one or more analyte concentrations) wirelessly (e.g., via a Bluetooth™ communication standard such as, for example and without limitation Bluetooth Low Energy) to a primary display device 130 (e.g., smartphone, tablet, laptop, personal computer, iPod, or health monitoring watch).

Figure 3:
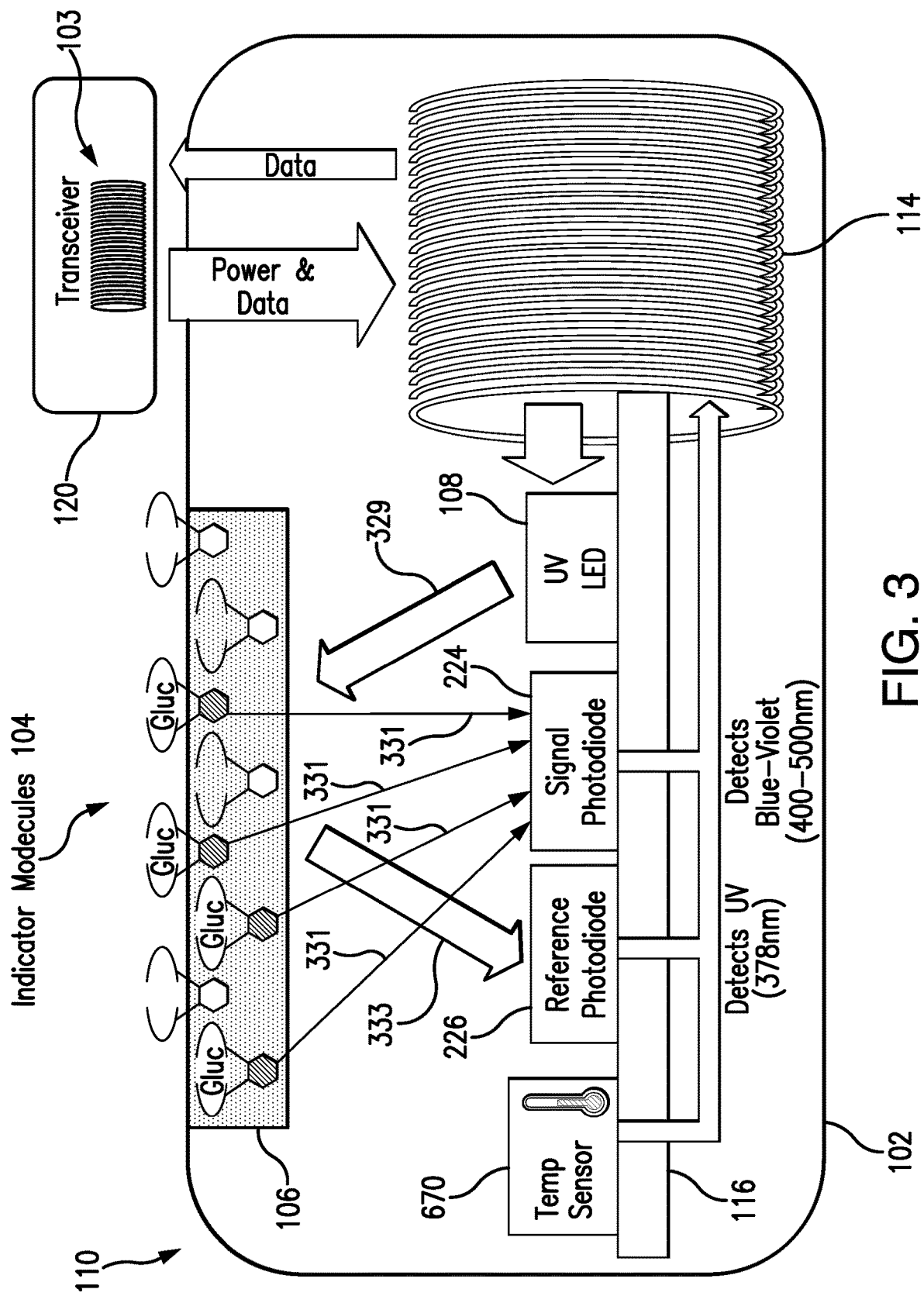
FIG. 3 is a schematic view illustrating a sensor and transceiver of an analyte monitoring system embodying aspects of the present invention.

In some embodiments, as illustrated in FIG. 3, the transceiver 120 may include an inductive element 103, such as, for example, a coil. The transceiver 120 may generate an electromagnetic wave or electrodynamic field (e.g., by using a coil) to induce a current in an inductive element 114 of the sensor 110, which powers the sensor 110. The transceiver 120 may also convey data (e.g., commands) to the sensor 110. For example, in a non-limiting embodiment, the transceiver 120 may convey data by modulating the electromagnetic wave used to power the sensor 110 (e.g., by modulating the current flowing through a coil 103 of the transceiver 120). The modulation in the electromagnetic wave generated by the transceiver 120 may be detected/extracted by the sensor 110. Moreover, the transceiver 120 may receive sensor data (e.g., measurement information) from the sensor 110. For example, in a non-limiting embodiment, the transceiver 120 may receive sensor data by detecting modulations in the electromagnetic wave generated by the sensor 110, e.g., by detecting modulations in the current flowing through the coil 103 of the transceiver 120.

The inductive element 103 of the transceiver 120 and the inductive element 114 of the sensor 110 may be in any configuration that permits adequate field strength to be achieved when the two inductive elements are brought within adequate physical proximity.

In some non-limiting embodiments, as illustrated in FIG. 3, the sensor 110 may be encased in a sensor housing 102 (i.e., body, shell, capsule, or encasement), which may be biocompatible. The sensor 110 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 110 may include indicator molecules 104 (e.g., fluorescent indicator molecules) exhibiting one or more detectable properties (e.g., optical properties) based on the amount or concentration of the analyte in proximity to the analyte indicator element 106. In some embodiments, the sensor 110 may include a light source 108 that emits excitation light 329 over a range of wavelengths that interact with the indicator molecules 104. The sensor 110 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 110 may include a temperature transducer 670. In some non-limiting embodiments, the sensor 110 may include a drug-eluting polymer matrix that disperses one or more therapeutic agents (e.g., an anti-inflammatory drug).

In some embodiments, as illustrated in FIG. 3, the sensor 110 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry being secured to the semiconductor substrate 116 and/or a core (e.g., ferrite core) for the inductive element 114. In some embodiments, the semiconductor substrate 116 and/or a core may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 110 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 110 and/or transceiver 120 may be as described in one or more of U.S. application Ser. Nos. 13/761,839, 13/937,871, and 13/650,016.

Figure 2:
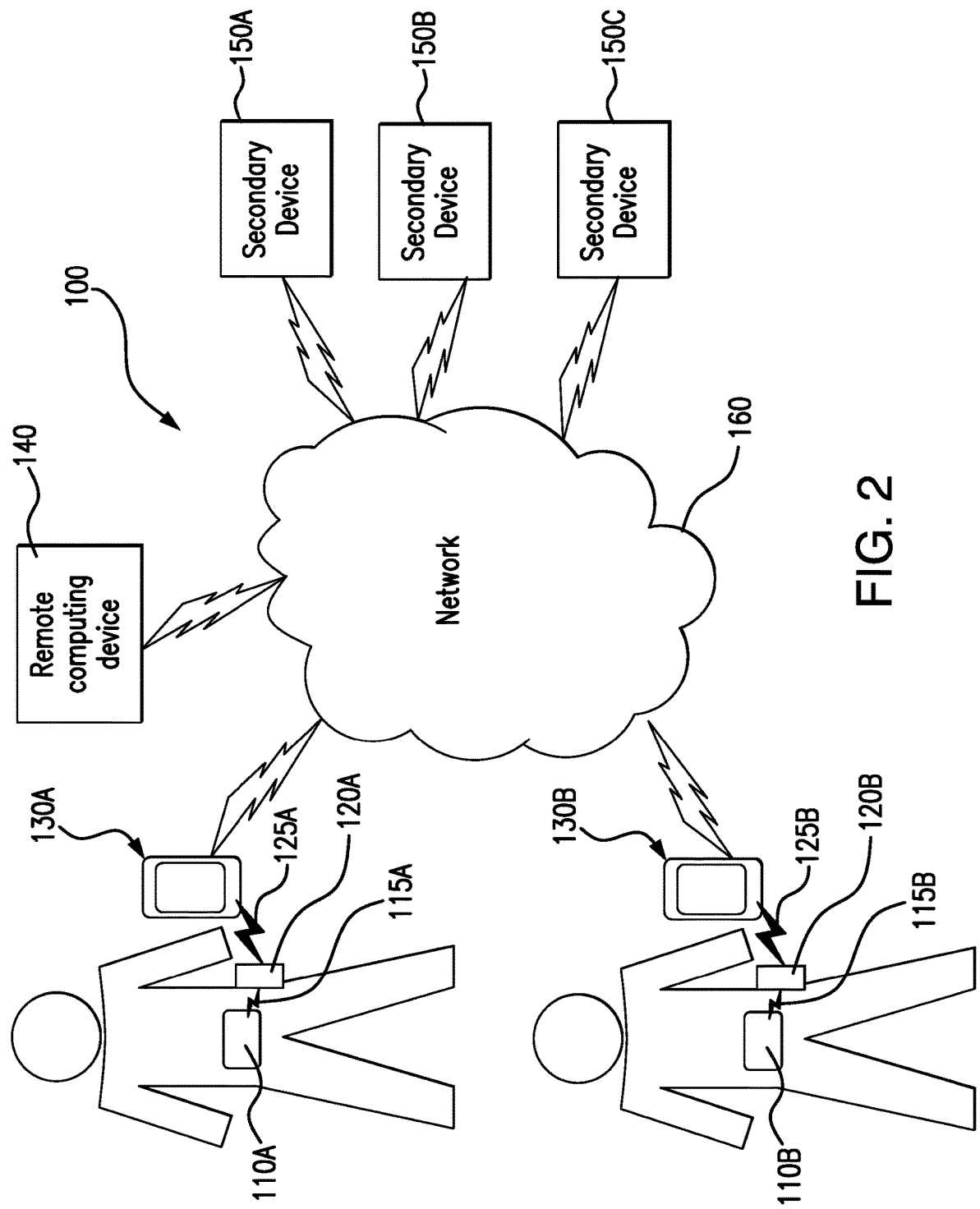
FIG. 2 is a schematic view illustrating an analyte monitoring system embodying aspects of the present invention.

Although in some embodiments, as illustrated in FIG. 3, the sensor 110 may be an optical sensor, this is not required, and, in one or more alternative embodiments, sensor 110 may be a different type of analyte sensor, such as, for example, an electrochemical sensor, a diffusion sensor, or a pressure sensor. Also, although in some embodiments, as illustrated in FIGS. 1 and 2, the analyte sensor 110 may be a fully implantable sensor, this is not required, and, in some alternative embodiments, the sensor 110 may be a transcutaneous sensor having a wired connection to the transceiver 120. For example, in some alternative embodiments, the sensor 110 may be located in or on a transcutaneous needle (e.g., at the tip thereof). In these embodiments, instead of wirelessly communicating using inductive elements 103 and 114, the sensor 110 and transceiver 120 may communicate using one or more wires connected between the transceiver 120 and the transceiver transcutaneous needle that includes the sensor 110. For another example, in some alternative embodiments, the sensor 110 may be located in a catheter (e.g., for intravenous blood glucose monitoring) and may communicate (wirelessly or using wires) with the transceiver 120.

In some embodiments, the sensor 110 may include a transceiver interface device. In some embodiments where the sensor 110 includes an antenna (e.g., inductive element 114), the transceiver interface device may include the antenna (e.g., inductive element 114) of sensor 110. In some of the transcutaneous embodiments where there exists a wired connection between the sensor 110 and the transceiver 120, the transceiver interface device may include the wired connection.

Figure 5:
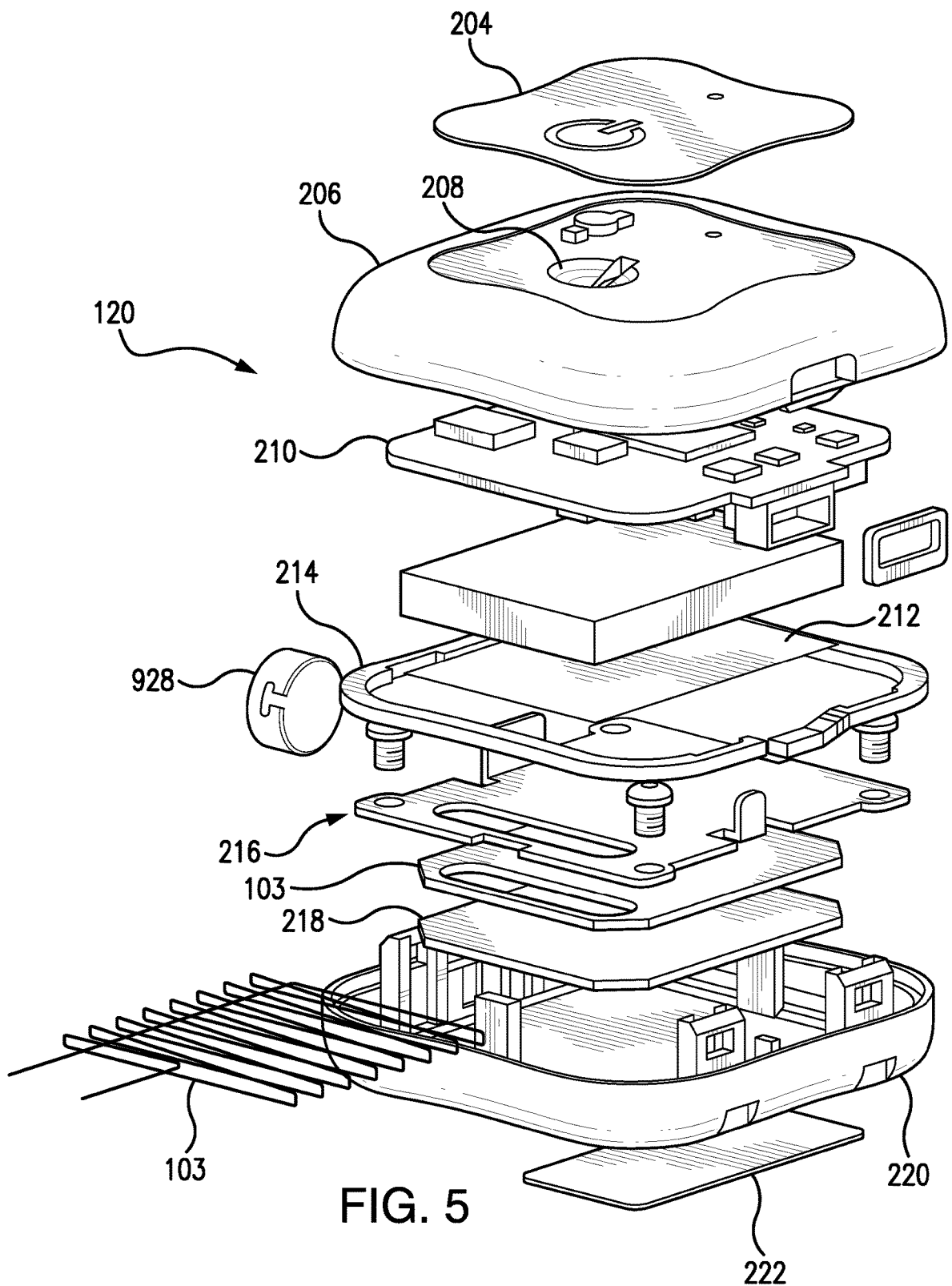
FIG. 5 is an exploded, perspective view of a transceiver embodying aspects of the invention.

FIGS. 5 and 5 are cross-sectional and exploded views, respectively, of a non-limiting embodiment of the transceiver 120, which may be included in the analyte monitoring system 100 illustrated in FIG. 1. As illustrated in FIG. 5, in some non-limiting embodiments, the transceiver 120 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 120 may be programmed and functionally tested. In some embodiments, assembled transceivers 120 may be packaged into their final shipping containers and be ready for sale.

Figure 4:
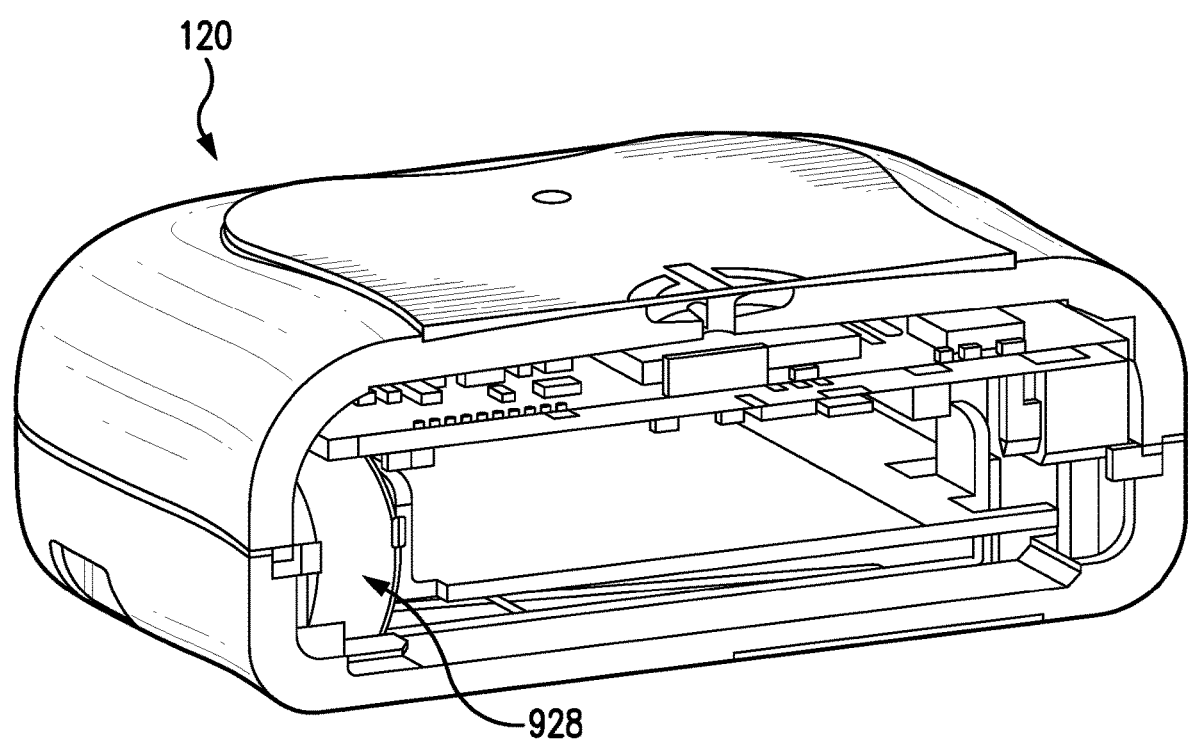
FIG. 4 is cross-sectional, perspective view of a transceiver embodying aspects of the invention.

In some embodiments, as illustrated in FIGS. 4 and 5, the antenna 103 may be contained within the housing 206 and 220 of the transceiver 120. In some embodiments, the antenna 103 in the transceiver 120 may be small and/or flat so that the antenna 103 fits within the housing 206 and 220 of a small, lightweight transceiver 120. In some embodiments, the antenna 103 may be robust and capable of resisting various impacts. In some embodiments, the transceiver 120 may be suitable for placement, for example, on an abdomen area, upper-arm, wrist, or thigh of a patient body. In some non-limiting embodiments, the transceiver 120 may be suitable for attachment to a patient body by means of a biocompatible patch. Although, in some embodiments, the antenna 103 may be contained within the housing 206 and 220 of the transceiver 120, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 6:
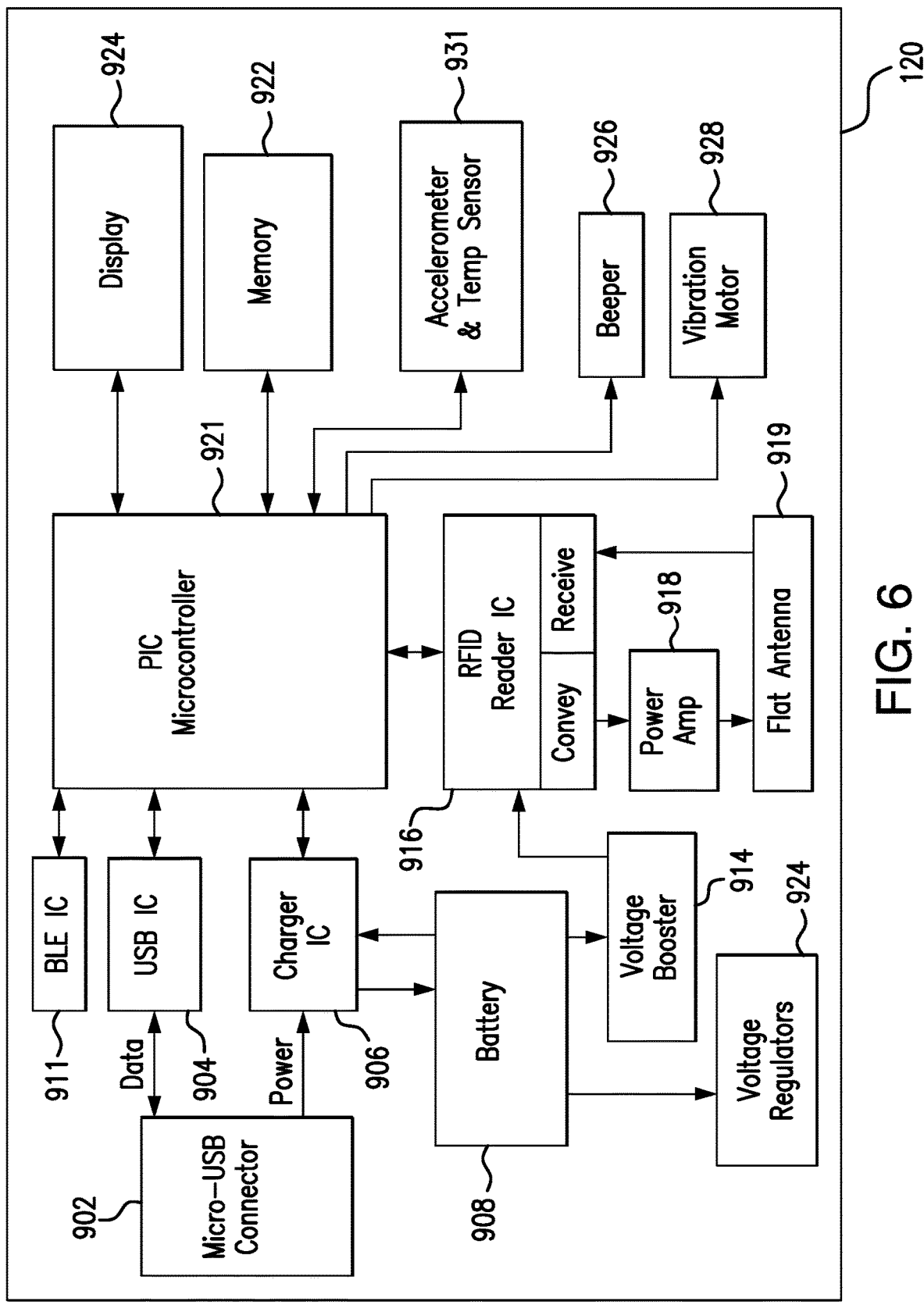
FIG. 6 is a schematic view illustrating a transceiver embodying aspects of the present invention.

FIG. 6 is a schematic view of an external transceiver 120 according to a non-limiting embodiment. In some embodiments, the transceiver 120 may have a connector 902, such as, for example, a Micro-Universal Serial Bus (USB) connector. The connector 902 may enable a wired connection to an external device, such as a personal computer (e.g., personal computer 109) or a primary display device 130 (e.g., a smartphone).

The transceiver 120 may exchange data to and from the external device through the connector 902 and/or may receive power through the connector 902. The transceiver 120 may include a connector integrated circuit (IC) 904, such as, for example, a USB-IC, which may control transmission and receipt of data through the connector 902. The transceiver 120 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 120 may include one or more connectors in addition to (or as an alternative to) Micro-USB connector 902. For example, in one alternative embodiment, the transceiver 120 may include a spring-based connector (e.g., Pogo pin connector) in addition to (or as an alternative to) Micro-USB connector 902, and the transceiver 120 may use a connection established via the spring-based connector for wired communication to a personal computer (e.g., personal computer 109) or a primary display device 130 (e.g., a smartphone) and/or to receive power, which may be used, for example, to charge the battery 908.

In some embodiments, the transceiver 120 may have a wireless communication IC 911, which enables wireless communication with an external device, such as, for example, one or more personal computers (e.g., personal computer 109) or one or more display devices 105 (e.g., a smartphone). In one non-limiting embodiment, the wireless communication IC 911 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 911 may be configured to wirelessly transmit data at a frequency greater than 1 gigahertz (e.g., 2.4 or 5 GHz). In some embodiments, the wireless communication IC 911 may include an antenna (e.g., a Bluetooth antenna). In some non-limiting embodiments, the antenna of the wireless communication IC 911 may be entirely contained within the housing (e.g., housing 206 and 220) of the transceiver 120. However, this is not required, and, in alternative embodiments, all or a portion of the antenna of the wireless communication IC 911 may be external to the transceiver housing.

In some embodiments, the transceiver 120 may include a display interface device, which may enable communication by the transceiver 120 with one or more display devices 105. In some embodiments, the display interface device may include the antenna of the wireless communication IC 911 and/or the connector 902. In some non-limiting embodiments, the display interface device may additionally include the wireless communication IC 911 and/or the connector IC 904.

In some embodiments, the transceiver 120 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 120 and receive information (e.g., measurement information) from the sensor 110. In some non-limiting embodiments, the sensor 110 and transceiver 120 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 120 may be in any configuration that permits adequate field strength to be achieved when brought within adequate physical proximity to the inductive element 114 of the sensor 110. In some embodiments, the transceiver 120 may include a power amplifier 918 to amplify the signal to be conveyed by the inductive element 103 to the sensor 110.

The transceiver 120 may include a peripheral interface controller (PIC) microcontroller 921 and memory 922 (e.g., Flash memory), which may be non-volatile and/or capable of being electronically erased and/or rewritten. The PIC microcontroller 921 may control the overall operation of the transceiver 120. For example, the PIC microcontroller 921 may control the connector IC 904 or wireless communication IC 911 to transmit data via wired or wireless communication and/or control the RFID reader IC 916 to convey data via the inductive element 103. The PIC microcontroller 921 may also control processing of data received via the inductive element 103, connector 902, or wireless communication IC 911.

In some embodiments, the transceiver 120 may include a sensor interface device, which may enable communication by the transceiver 120 with a sensor 110. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 110 and the transceiver 120 (e.g., transcutaneous embodiments), the sensor interface device may include the wired connection.

In some embodiments, the transceiver 120 may include a display 924 (e.g., liquid crystal display and/or one or more light emitting diodes), which PIC microcontroller 921 may control to display data (e.g., analyte concentration values). In some embodiments, the transceiver 120 may include a speaker 926 (e.g., a beeper) and/or vibration motor 928, which may be activated, for example, in the event that an alarm condition (e.g., detection of a hypoglycemic or hyperglycemic condition) is met. The transceiver 120 may also include one or more additional sensors 931, which may include, for example and without limitation, one or more of an accelerometer and a temperature sensor, that may be used in the processing performed by the PIC microcontroller 921.

In some embodiments, the transceiver 120 may be a body-worn transceiver that is a rechargeable, external device worn over the sensor implantation or insertion site. The transceiver 120 may supply power to the proximate sensor 110, calculate analyte concentrations from data received from the sensor 110, and/or transmit the calculated analyte concentrations to a primary display device 130 (see FIG. 1). Power may be supplied to the sensor 110 through an inductive link (e.g., an inductive link of 13.56 MHz). In some embodiments, the transceiver 120 may be placed using an adhesive patch or a specially designed strap or belt. The external transceiver 120 may read measured analyte data from a subcutaneous sensor 110 (e.g., up to a depth of 2 cm or more). The transceiver 120 may periodically (e.g., every 2, 5, or 10 minutes) read sensor data and calculate an analyte concentration and an analyte concentration trend. From this information, the transceiver 120 may also determine if an alert and/or alarm condition exists, which may be signaled to the user (e.g., through vibration by vibration motor 928 and/or an LED of the transceiver's display 924 and/or a display of a primary display device 130). The information from the transceiver 120 (e.g., calculated analyte concentrations, calculated analyte concentration trends, alerts, alarms, and/or notifications) may be transmitted to a primary display device 130 (e.g., via Bluetooth Low Energy with Advanced Encryption Standard (AES)-Counter CBC-MAC (CCM) encryption) for display by a mobile medical application (MMA) being executed by the primary display device 130. In some non-limiting embodiments, the MMA may provide alarms, alerts, and/or notifications in addition to any alerts, alarms, and/or notifications received from the transceiver 120. In one embodiment, the MMA may be configured to provide push notifications. In some embodiments, the transceiver 120 may have a power button (e.g., button 208) to allow the user to turn the device on or off, reset the device, or check the remaining battery life. In some embodiments, the transceiver 120 may have a button, which may be the same button as a power button or an additional button, to suppress one or more user notification signals (e.g., vibration, visual, and/or audible) of the transceiver 120 generated by the transceiver 120 in response to detection of an alert or alarm condition.

In some embodiments, the transceiver 120 of the analyte monitoring system 100 may receive sensor data conveyed from the analyte sensor 100. In some embodiments, the transceiver 120 may receive sensor data from the sensor 110 periodically (e.g., every 1, 2, 5, 10, 15, or 20 minutes). In some non-limiting embodiments, the sensor data may include one or more raw signals indicative of an amount or concentration of an analyte in a medium (e.g., interstitial fluid (ISF)) in proximity to the analyte indicator element 106 of the analyte sensor 110. In some embodiments, the raw signals may include one or more measurements (e.g., one or more measurements indicative of the level of emission light 331 from the indicator molecules 104 as measured by the photodetector 224, one or more measurements indicative of the level of reference light 333 as measured by photodetector 226, and/or one or more temperature measurements as measured by the temperature transducer 670).

In some embodiments, the transceiver 120 may calculate analyte information (e.g., a blood analyte level) using at least the received sensor data. In some non-limiting embodiments, the transceiver 120 may use the received raw signals to calculate an ISF analyte level. In some non-limiting embodiments, the transceiver 120 may use at least the calculated ISF analyte level to calculate a blood analyte level (e.g., by performing a lag compensation). In some embodiments, the transceiver 120 may store the analyte information (e.g., in memory 922). In some embodiments, the analyte information may be associated with a time stamp indicative of the time at which (a) the transceiver 120 conveyed a measurement command to the sensor 110, (b) the sensor 110 made the one or more measurements included in the sensor data, (c) the time at which the transceiver 120 received the sensor data used to calculate the analyte information, (d) the transceiver 120 calculated the measurement information, or (e) the transceiver 120 stored the analyte information. In some non-limiting embodiments, the analyte information may include an analyte level and one or more of the associated time stamp, health data (e.g., temperature), notifications, alerts, alarms, and analyte level trend information. In some embodiments, the transceiver 120 may be configured to convey the analyte information to the primary display device 130.

In some embodiments, one or more of the primary display device 130, the remote computing device 140, and one or more of the secondary display devices 150A-C may be connected to a network 160. In some embodiments, the network 160 may include, for example and without limitation, one or more of a local area network (LAN), a wide area network (WAN), the Internet, intranets, and a cellular network. In some embodiments, the primary display device 130 may configured to receive the analyte information conveyed from the transceiver 120. In some embodiments, the primary display device 130 may be configured to display the received analyte information. In some embodiments, the primary display device 130 may be configured to convey the analyte information over the network 160. In some embodiments, the remote computing device 140 may be configured to receive the analyte information conveyed from the primary display device 130 over the network 160. In some embodiments, the remote computing device 140 may include one or more servers. In some embodiments, one or more secondary display devices 150 may be configured to receive the analyte information from the remote computing device 140 over the network 160 and to display the received analyte information. In some embodiments, the one or more secondary display devices 150 may be, for example and without limitation, one or more of smartphones, tablets, laptops, personal computers, iPods, and health monitoring watches. In this way, the primary display device 130 may share analyte information with one or more secondary display devices 150. In some embodiments, the primary display device 130 may share analyte information with one or more identified groups, such as a circle of concern (e.g. people who may have an interest in monitoring data for a patient), specific devices (e.g. web apps, servers, data storage, and/or the like), specific applications (e.g. applications configured to process specific data), and/or the like.

In some alternative embodiments, the primary display device 130 may additionally perform some or all of the functions of the transceiver 120. In some alternative embodiments, the primary display device 130 may communicate directly with the analyte sensor 110. In some embodiments, the primary display device 130 may convey commands (e.g., measurement commands) to the analyte sensor 110. In some embodiments, the analyte monitoring system 100 may not include a transceiver 120. In some embodiments, the primary display device 130 (instead of or in addition to a transceiver 120) may receive sensor data conveyed from the analyte sensor 110 and calculate analyte information using at least the received sensor data. In some embodiments, the primary display device 130 and the analyte sensor 110 may communicate using NFC (e.g. at a frequency of 13.56 MHz). In some embodiments, the primary display device 130 may include an inductive element (e.g. flat antenna, loop antenna, etc.) that is configured to permit adequate field strength to be achieved when brought within adequate physical proximity to the inductive element 114 of the sensor 110. In some non-limiting embodiments, the primary display device 130 may receive sensor data from the sensor 110 periodically (e.g., every 1, 2, 5, 10, 15, or 20 minutes). In some non-limiting embodiments, the primary display device 130 may receive sensor data from the sensor 110 on demand (e.g., when the primary display device 130 is swiped in proximity to the sensor 110). In some non-limiting embodiments, the primary display device 130 may include a sensor interface device, which may enable communication by the primary display device 130 with a sensor 110. In some embodiments, the sensor interface device may include the inductive element. In some non-limiting embodiments, the sensor interface device may additionally include the RFID reader IC 916 and/or the power amplifier 918 described above with reference to FIG. 6.

In some embodiments, the primary display device 130 may receive measured analyte data from an analyte sensor 110. The primary display device 130 may calculate an analyte concentration and an analyte concentration trend using at least the received sensor data. From this analyte information, the primary display device 130 may also determine if an alert and/or alarm condition exists, which may be signaled to the user (e.g., through vibration by a vibration motor and/or a display of a primary display device 130). In some embodiments, this analyte information (e.g., calculated analyte concentrations, calculated analyte concentration trends, alerts, alarms, and/or notifications) may be displayed by a MMA being executed by the primary display device 130. In some embodiments, the primary display device 130 may transmit this information (e.g., calculated analyte concentrations, calculated analyte concentration trends, alerts, alarms, and/or notifications) over a network 160 such that a remote computing device 140 and one or more secondary display devices 150 may receive, store, and display the analyte information.

Although only one sensor, transceiver, and primary display device set is shown in FIG. 1, the analyte monitoring system 100 may include multiple sensor, transceiver, and primary display device sets. For example, as shown in FIG. 2, the analyte monitoring system 100 may include a first analyte sensor 110A, a first transceiver 120A, and a first primary display device 130A. The analyte monitoring system 100 may also include a second analyte sensor 110B, a second transceiver 120B, and a second primary display device 130B. Although not shown in FIG. 2, the analyte monitoring system 100 may include additional (e.g., third, fourth, fifth, . . . one thousandth, etc.) sensor, transceiver, and primary display device sets.

Consistent with the description of the analyte sensor 110, transceiver 120, and primary display device 130 of FIG. 1, the first analyte sensor 110A may be configured to convey first sensor data indicative of a level of analyte in a medium in proximity to the first analyte sensor 110A. The first transceiver 120A may configured to receive the first sensor data conveyed from the first analyte sensor 110A, calculate first analyte information using at least the received first sensor data, and convey the first analyte information. The first primary display device 130A may be configured to receive the first analyte information conveyed from the first transceiver 120A, display the received first analyte information, and convey the first analyte information over the network 160. In some embodiments, the first analyte sensor 110A may be in communication with the first transceiver 120A over a first communication link 115A, and the first transceiver 120A may be in communication with the first primary display device 130A over a second communication link 125A.

Consistent with the description of the analyte sensor 110, transceiver 120, and primary display device 130 of FIG. 1, the second analyte sensor 110B may be configured to convey second sensor data indicative of a level of analyte in a medium in proximity to the second analyte sensor 110B. The second transceiver 120B may configured to receive the second sensor data conveyed from the second analyte sensor 110B, calculate second analyte information using at least the received second sensor data, and convey the second analyte information. The second primary display device 130B may be configured to receive the second analyte information conveyed from the second transceiver 120B, display the received second analyte information, and convey the second analyte information over the network 160. In some embodiments, the second analyte sensor 110B may be in communication with the second transceiver 120B over a first communication link 115B, and the second transceiver 120B may be in communication with the second primary display device 130B over a second communication link 125B.

In some embodiments, the remote computing device 140 may be configured to receive the first analyte information conveyed from the first primary display device 130A over the network 160 and to receive the second analyte information conveyed from the second primary display device 130B over the network 160. A secondary display device 150 may be configured to receive one or more of the first analyte information and the second analyte information from the remote computing device 140 over the network 160 and to display one or more of the first and second analyte information.

Figure 7:
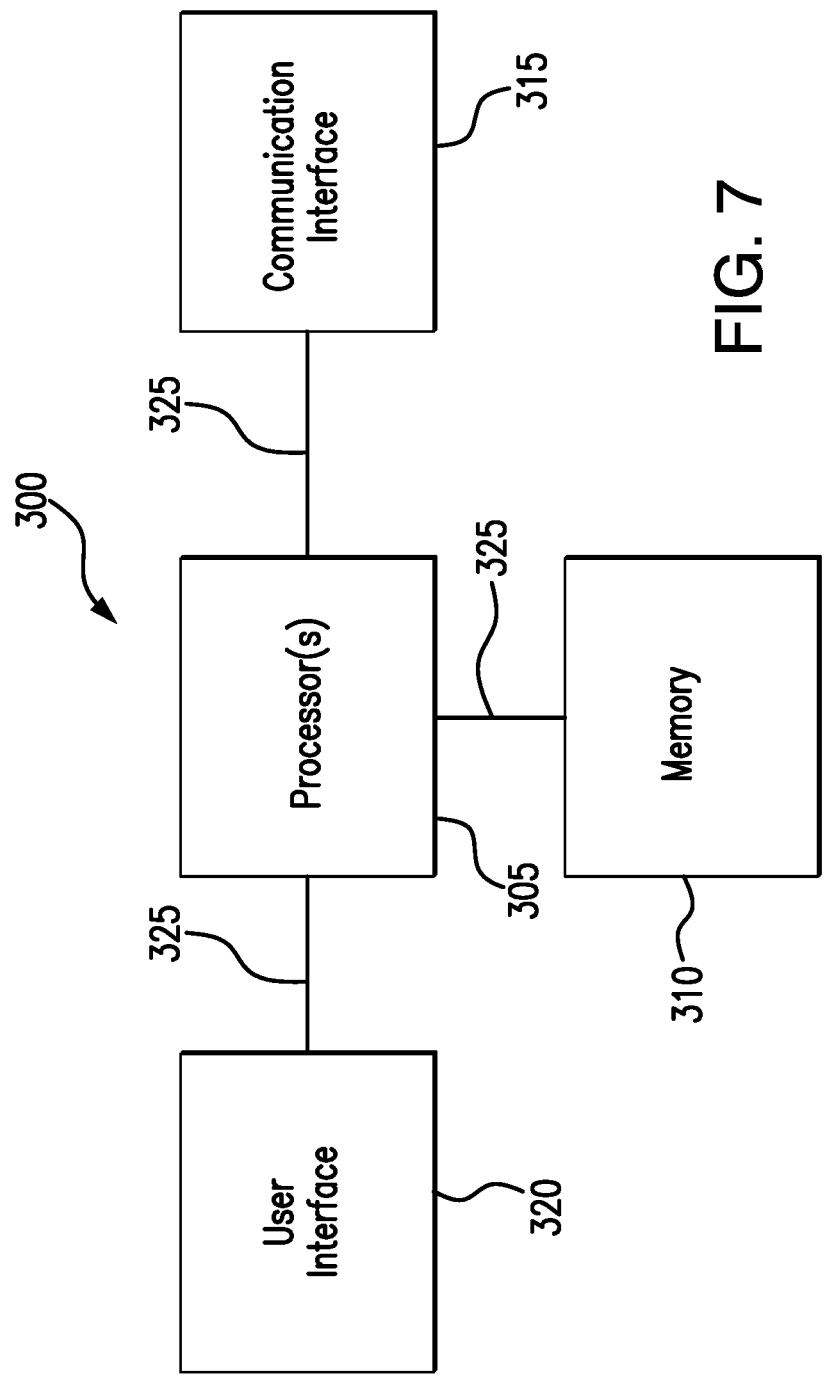
FIG. 7 is a schematic view illustrating a processing system of a display device embodying aspects of the present invention.

In some embodiments, one or more of the primary and secondary display devices 130 and 150 may include a processing system. FIG. 7 illustrates an example of a processing system 300 that may be included in a primary or secondary display device 130 or 150. As shown in FIG. 7, the processing system 300 may include one or more processors 305, a memory 310, a communication interface 315, a user interface 320, and/or a bus 325 that couples the various processing system components including the memory 310 to the one or more processors 305. The one or more processors 305 may include of one or more central processing units (CPUs) that execute computer program instructions stored in the memory 310 to perform functions described herein with respect to the one or more of the primary and secondary display devices 130 and 150. These functions may be configured to improve the technological field of analyte monitoring. In some embodiments, the memory 310 may include computer storage media in the form of volatile and/or nonvolatile memory, such as ROM and RAM. The system memory 310 may further include non-removable nonvolatile computer storage media, such as a hard disk drive or removable nonvolatile computer storage media that is configured to read from a flash drive, optical disk drive, or other optical media. The drives and their associated computer storage media may provide storage of computer readable instructions, data structures, program modules and other data for the processing system, which are inputted to the one or more processors for the performance of particular tasks.

In some embodiments, the user interface 320 of the processing system 300 may enable an operator to control the device by providing one or more input and/or output devices. The input and/or output devices may include, for example and without limitation, one or more of push-button(s), a keyboard, a microphone, a camera, a pointing device (e.g., a mouse, trackball, or touch pad), touch screen(s), voice interfaces(s), multimedia interface(s), audio interface(s), tactile interfaces(s), visual interface(s), and monitor(s). Accordingly, a user may enter commands and information into the device through input devices, and the device may present the analyte information to the user via the output devices.

In some embodiments, the communication interface 315 of the processing system 300 may enable the display device to communicate with one or more other devices of the analyte monitoring system.

Mobile Medical Applications

Figure 8:
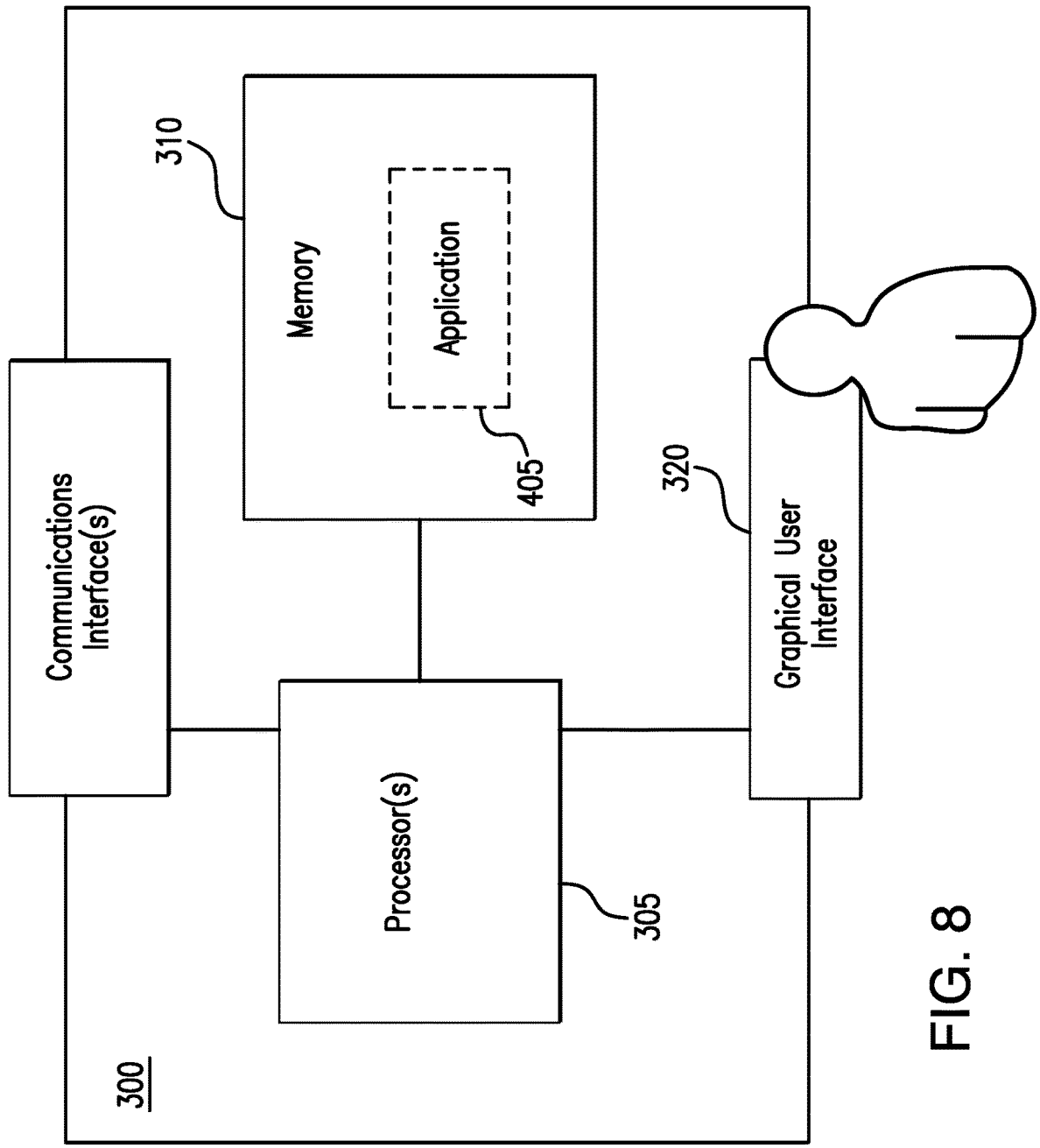
FIG. 8 is a schematic view illustrating a processing system of a display device embodying aspects of the present invention.

In some embodiments, as shown in FIG. 8, the memory 310 may store an application 405 in the form of computer readable instructions. In some non-limiting embodiments, the application 405 may be a mobile medical application ("MMA"). In some embodiments, the one or more processors 305 may be configured to execute one or more of the computer readable instructions of the application 405. In some embodiments, the application 405 on a primary display device 130 may be a patient application. In some embodiments, the patient application may be configured to allow a user of the primary display device 130 to share analyte information with one or more secondary display devices 150. In some embodiments, the application 405 on a secondary display device 150 may be an observer application. In some embodiments, the observer application may be configured to allow a user of the secondary display device 150 to receive and view analyte information from one or more primary display devices 130.

In some embodiments, where the application 405 may cause the display device to provide a series of graphical control elements or widgets, such as a graphical user interface (GUI), shown on the display of the user interface 320. In some embodiments, the application 405 may, for example and without limitation, cause the display device 130 or 150 to display analyte related information in a GUI such as, but not limited to: one or more of analyte information, current analyte readings, user notifications, analyte status alerts and alarms, trend graphs and arrows, and user-entered events, and may provide one or more graphical control elements that may allow a user to manipulate aspects of the one or more display screens. Although aspects of the application 405 are described in the context of glucose monitoring system embodiments below, this is not required, and, in some alternative embodiments, the application 405 may be employed in other types of analyte monitoring systems.

In some embodiments, the application 405 may be configured to allow a primary display device 130 to share analyte information with one or more secondary display devices 150. In some embodiments, a user of a primary display device may be a patient, and a user of a secondary display device may be an observer. The analyte monitoring system 100 may be monitoring analyte levels of the patient, and the observer may be someone having an interest in monitoring the data of the patient, such as, for example and without limitation, a caregiver, a physician, a health care provider, a research group member, or a family member (e.g., parent). A primary display device 130 and a secondary display device 150 may be linked together over the network 160 of the analyte monitoring system 100. In some embodiments, a patient application may be stored as computer readable instructions in the memory of a primary display device 130, and an observer application is stored as computer readable instructions in the memory of a secondary display device 150. The patient application may be configured to allow a user of the primary display device to share analyte information obtained from the analyte sensor to the secondary display device of the analyte monitoring system. The observer application configured to allow a user of the secondary display device to receive and view the shared analyte information from the primary display device. In some embodiments, the shared analyte information from a primary display device 105 may be first transmitted to a remote computing device 140, such as a server, and the observer application is configured to allow a user of a secondary display device 150 to access the shared analyte information stored on the remote computing device 140. Accordingly, an observer operating a secondary display device 150 may follow and keep track of the analyte information of the patient.

In some embodiments, the analyte monitoring system 100 may include a plurality of secondary display devices 150 corresponding to an identified group of observers. In some embodiments, a patient application may be configured to allow a user of the primary display device 130 to share the analyte information with one or more secondary display devices 150 over the network 160 so that each observer in the identified group can view the shared analyte information on a respective secondary display device 150. An observer application being executed on the secondary display device 150 of an observer in the identified group may be configured to enable the observer to view of the shared analyte information. In one embodiment, the shared analyte information obtained from the primary display device is first transmitted to a remote computing device 140, such as a server, and observer applications may be configured to allow a user of each secondary display device 150 to access the shared analyte information stored on the remote computing device 140. In some embodiments, the remote computing device 140 may be configured to restrict a secondary display device 150 from gaining access to analyte information stored on the remote computing device 140 by requiring a security credential, such as, for example and without limitation, a password or security token.

In some embodiments, the analyte monitoring system 100 may include a plurality of primary display devices 130 corresponding to an identified group of patients. An observer application may be configured to allow a user of a secondary display device 150 to receive analyte information from one or more primary display devices 130 over the network 160 so that the user of the secondary display device 150 can view analyte information obtained from each patient of the identified group. In one embodiment, the shared analyte information obtained from the primary display devices 130 may be first transmitted to a remote computing device 140, such as a server, and the observer application may be configured to allow a user of the secondary display device 150 to access the shared analyte information of the primary display devices 130 stored on the remote computing device 140.

In some embodiments, the analyte monitoring system 100 may include both a plurality of primary display devices 130 corresponding to an identified group of patients and a plurality of secondary display devices 150 corresponding to an identified group of observers. The patient application in the primary display devices 130 may be configured to allow a user of the primary display device to share the analyte information obtained from a respective analyte sensor with secondary display devices 150 so that each observer of the identified group can view the shared analyte information on a respective secondary display device 150. The observer application in each secondary display device 150 may be configured to allow a user of the secondary display device 150 to receive analyte information from primary display devices 130 so that the user of the secondary display device 150 can view analyte information from each patient of the identified group.

In some embodiments, the patient application may include a "share my data" setting to enable or disable sharing of analyte information with other secondary display devices of the analyte monitoring system. For example, the patient application may maintain a list of one or more members with whom data may be shared and their associated contact information, such as email addresses, telephone number, social media account. If the "share my data" setting is enabled, the patient application may be configured to allow the primary display device 130 to transmit shared information to one or more secondary display devices 150 over the network using, for example, one or more simple mail transfer protocol (SMTP) messages, short message service (SMS) messages, social media (e.g., Twitter) messages, enhanced messaging service (EMS) messages, or telephonic messages. For example, the patient application may authorize a secondary display device 150 to access to an identified group of observers by sending an email invitation to the secondary display device 150 over the network. Furthermore, once the "share my data" setting is enabled, the patient application may be configured to allow the primary display device 130 to share CGM data, such as glucose and trend graph and/or CGM notifications, alerts, and alarms, to the identified group of observers.

Figure 9:
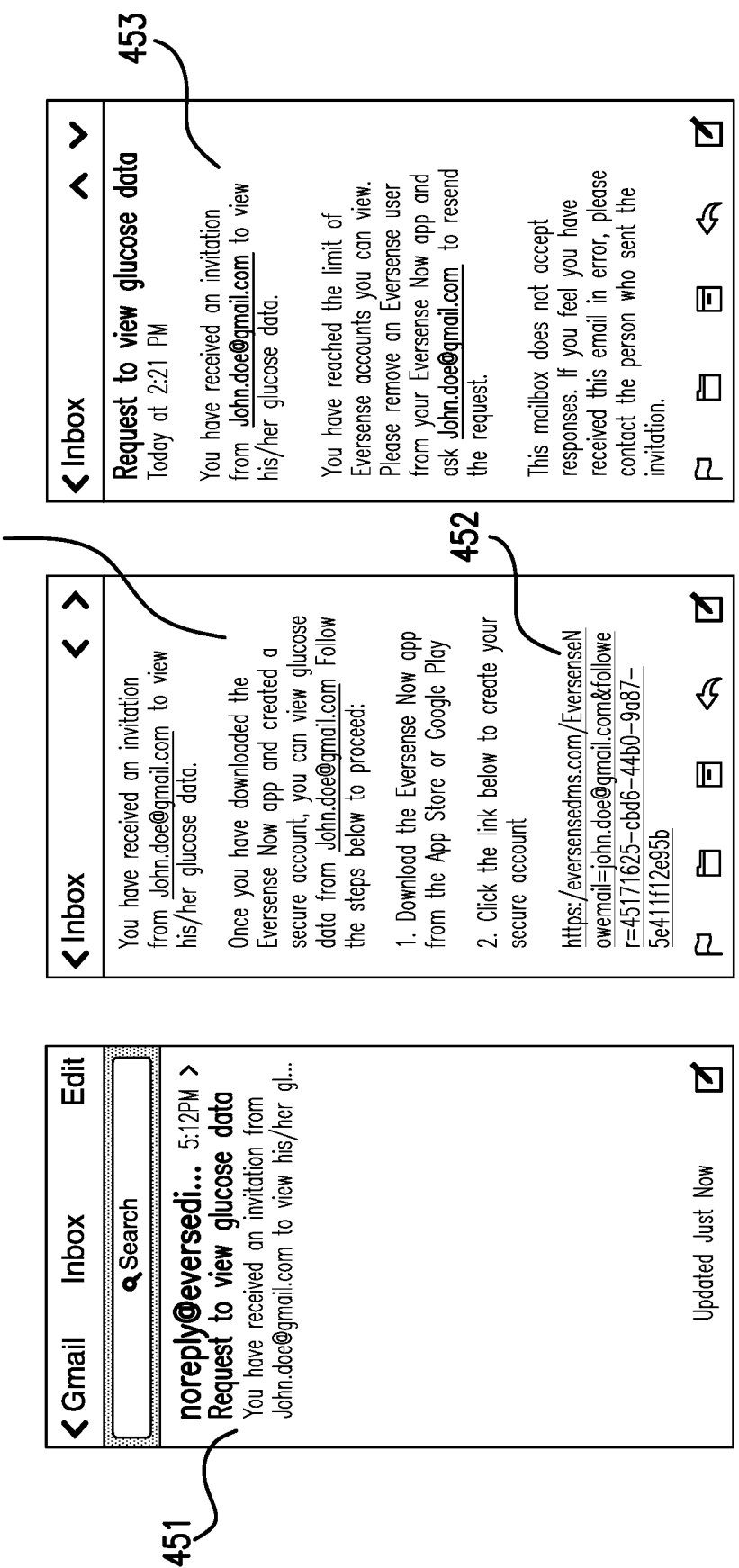
FIG. 9 shows an example invitation page in the form of an email message embodying aspects of the present invention.

In one embodiment, as shown in FIG. 9, a user may need to receive an invitation 450 from a patient to join an identified group of observers who are remotely monitoring the analyte data of the patient. For example, in some non-limiting embodiments, the user may receive an email invitation 451 from the patient with a request to view the analyte data of the patient. The email invitation 451 may include instructions for the user and a link 452 that allows the user to load the observer application on the secondary display device 150. A user may accept the invitation by clicking the link 452 and downloading the observer application into the memory of the secondary display device 150.

Figure 10:
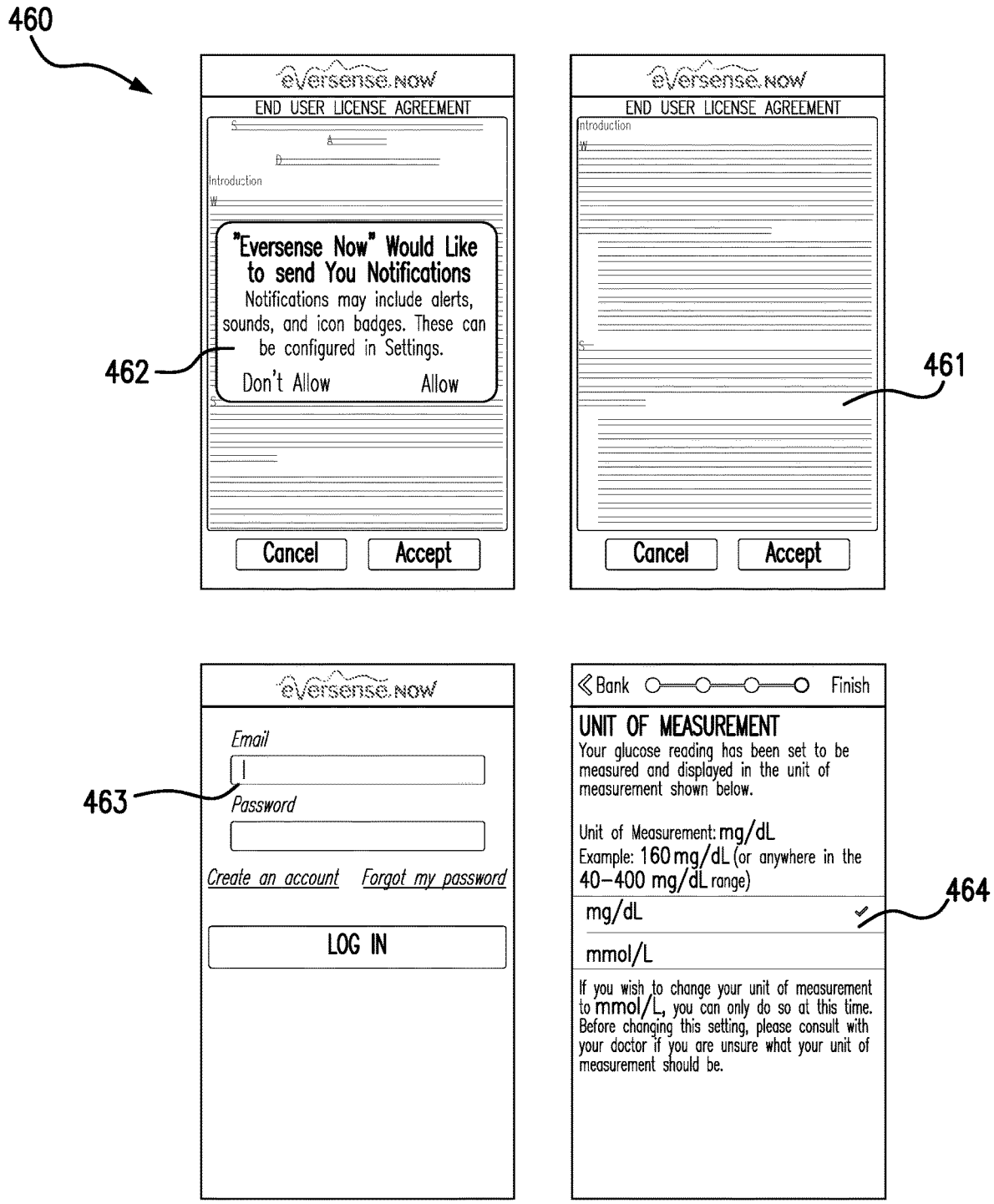
FIG. 10 shows an example registration page of the Eversense Now Application embodying aspects of the present invention.

In some embodiments, as shown in FIG. 10, after the observer application has been loaded into the memory of the second display device, the observer application may be configured to generate a notification 462 asking for the user's permission to receive alerts generated by the observer application. In some embodiments, the observer application may be configured to, after the user accepts permission, generate an end user license agreement 461 and request that the user accept the terms of the agreement 461. In some embodiments, the observer application may be configured to, after the user accepts the terms of the agreement 461, generate a registration page 463 where the user may create an account by designating an account name, such as the user's email, and password. In some embodiments, the observer application may be further configured to generate a unit of measurement screen 464 requesting the user to select which unit of measurement to be displayed under the analyte readings and the trend graphs. In one non-limiting example, the observer application may be configured to enable a user to select between two different units of measurements, such as "mg/dL" and "mmol/L." In some alternative examples, the observer application may be configured to enable a user to select between three different units of measurements.

In some embodiments, as shown in FIG. 9, after loading the observer application into the memory of a secondary display device 150 and creating a user account through the observer application, the user may select a link in the email invitation 450 so that the user account becomes part of a circle of concern for the patient. The circle of concern may be the identified group of observers who are remotely monitoring the analyte data of the patient. Accordingly, in some embodiments, the user may receive CGM data, notifications, alerts, and alarms with respect to a patient account via the observer application residing in the secondary display device 150.

In some embodiments, the observer application may be configured to limit the number of patients that an observer may monitor on the secondary display device 150. For example and without limitation, the observer application may set the maximum number of patients monitored by an observer to ten. In some embodiments, as shown in FIG. 9, if the observer receives an invitation from a patient, the observer application may be configured to determine whether the observer is already following the maximum number of patents. In some embodiments, the observer application may be configured to, if the observer is already following the maximum number of patents, generate an email 453 on the secondary display device 150 indicating that the observer has reached the limit as to the number of patients that may be monitored by the observer application. In some non-limiting embodiments, the email 453 may further instruct the observer to remove a patient already monitored by the observer application and to request that the new patient resend the invitation.

Main Menu Screen

Figure 11:
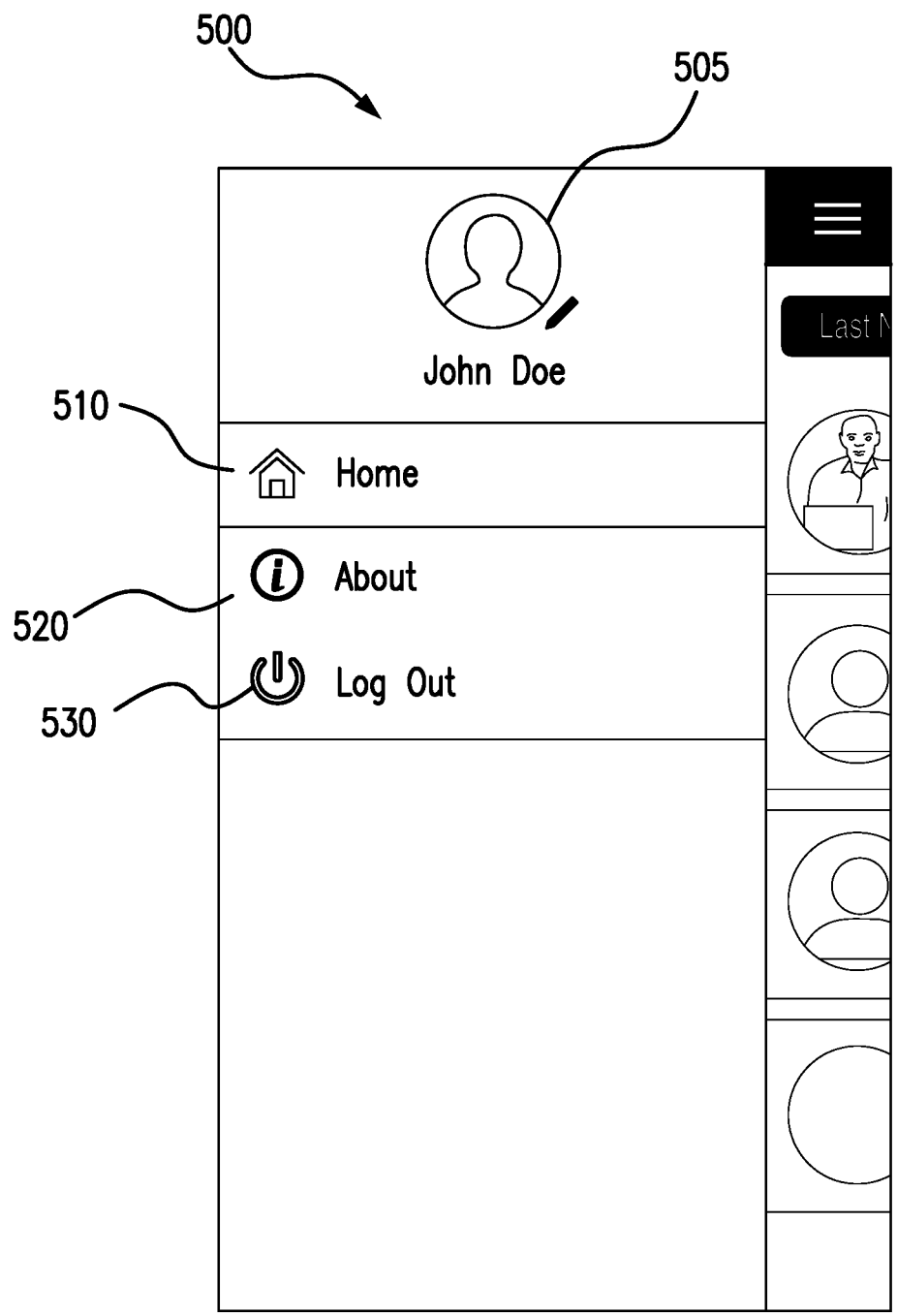
FIG. 11 shows an example menu screen embodying aspects of the present invention.

FIG. 11 shows an example of a menu screen generated by the observer application for display on a GUI of a secondary display device 150 in accordance to an embodiment of the present invention. When a user first gains access to his or her user account, the observer application may configure the secondary display device 150 to present the menu screen on a display of the secondary display device 150. As shown in FIG. 11, the menu screen may display one or more of the name of the user account 505, a home icon 510, an about icon 520, and a log out icon 530. A user may gain access to a home screen of the observer application by selecting the home icon 510. A user may gain access to the about screen of the observer application by selecting the about icon 520. A user may exit from his or her user account by selecting the log out icon 530.

Home Screen

Figure 12A:
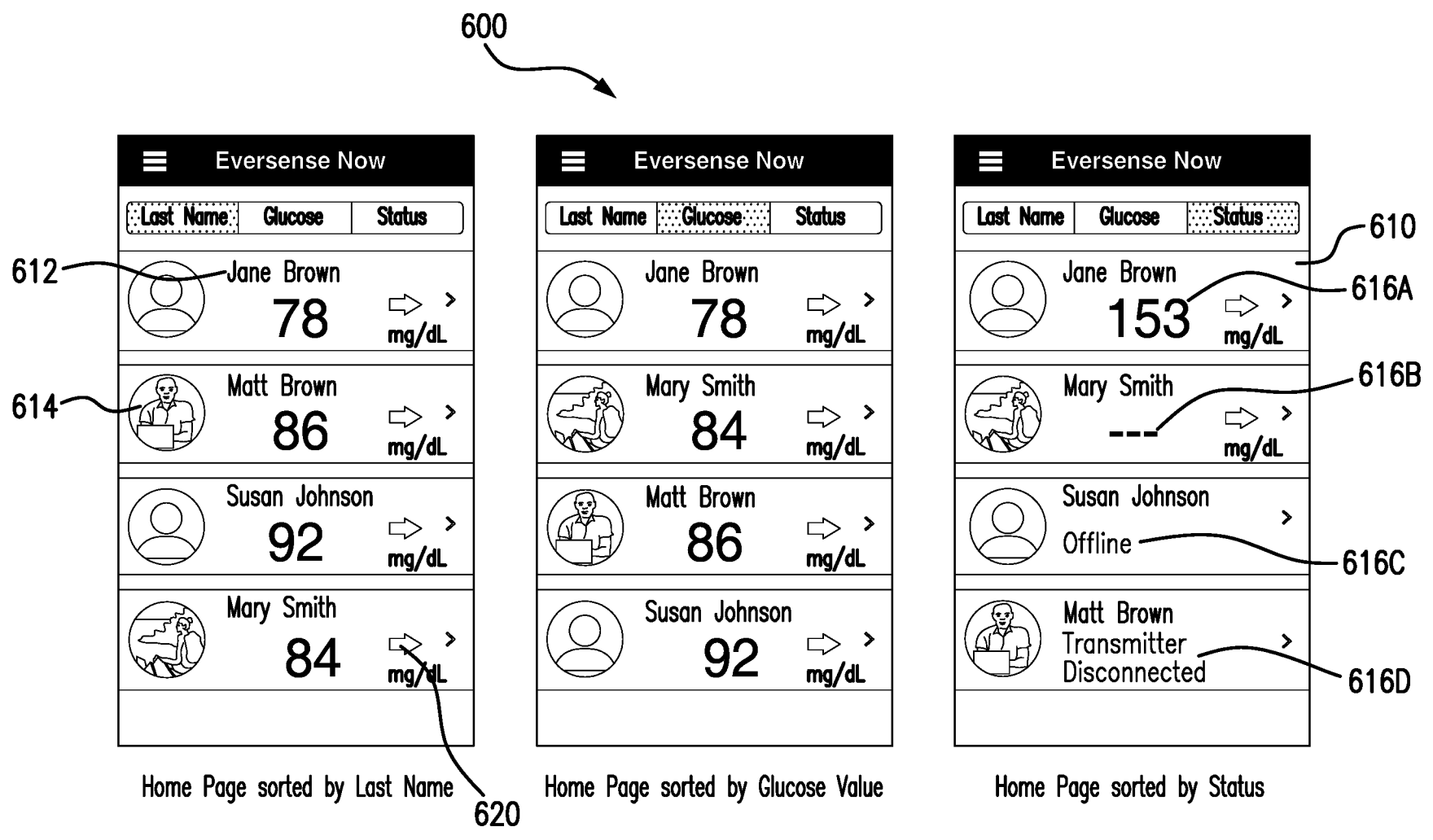
Figure 12B:
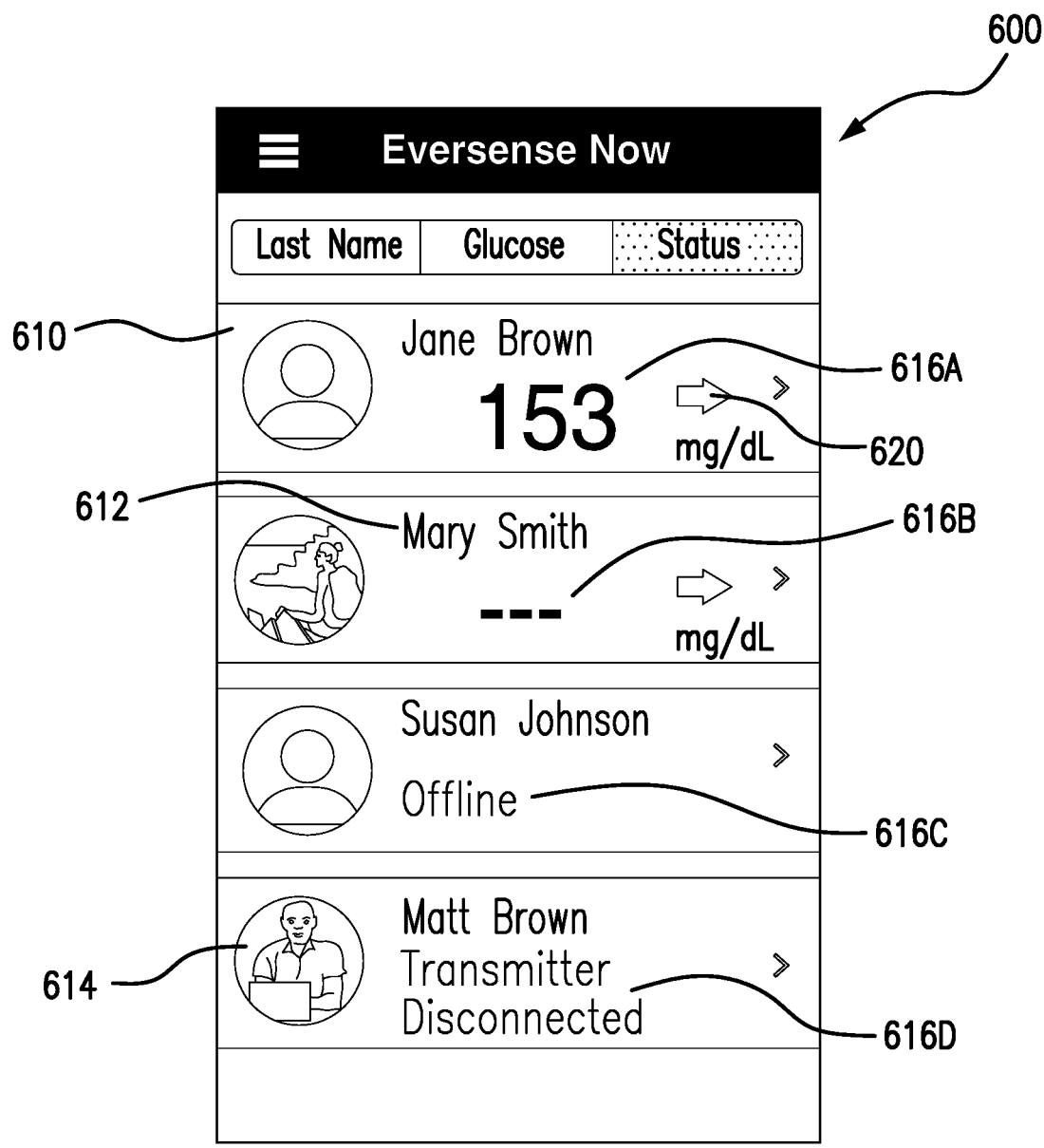
Figure 12C:
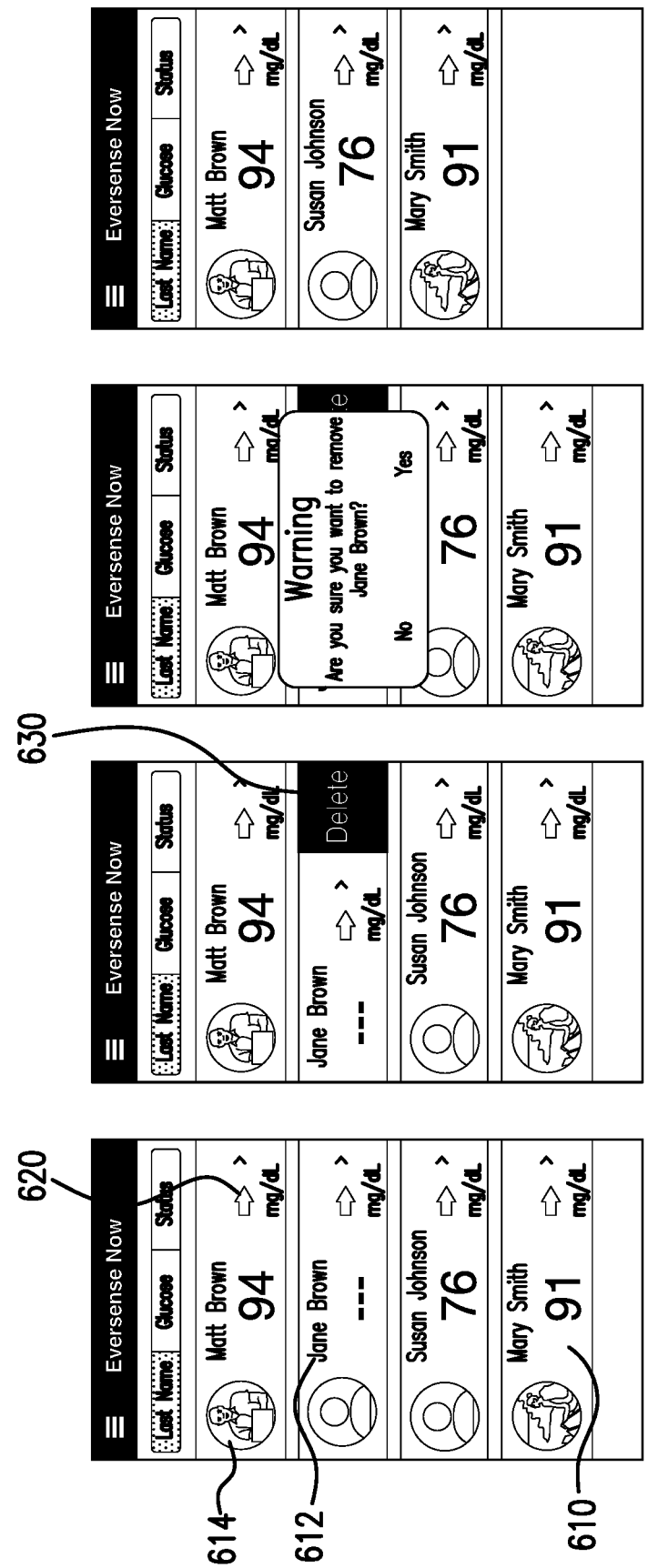

FIGS. 12A and 12B show a non-limiting example of a home screen 600 generated by the observer application for display on a GUI of a secondary display device 150 in accordance to various embodiments of the present invention. The home screen 600 may display a list of patient accounts whose analyte information is followed by the observer application. As shown in FIG. 12A, in some embodiments, each patient account may be represented by a patient bar 610, in which the patient bar may depict one or more of a name of the patient 612, a photograph of the patient 614, a status of the patient account 616, a current glucose level of a patient 618, and a trend arrow 620 reflecting a rate and/or direction of change in glucose measurement of a patient. In some embodiments, the list of patient bars 610 may be sorted by different criteria, such as alphabetical order as to the last names of the patient, the glucose value of the patients, or the status of the patient. In some embodiments, a user may remove a patient account from the list of patient bar. For example, in some embodiments, as shown in FIG. 12C, a user may select and move the desired patient bar 610 towards the left on the display of the device to generate a "delete" icon 630. Consequently, the user may remove the patient account by the selecting the "delete" icon 630.

In some embodiments, as shown in FIG. 12B, the status of the patient account may be categorized as being in a particular condition. In some embodiments, the conditions may include one or more of active, incomplete, offline, and disconnected. In some embodiments, in an active status, the patient bar may display the most recent glucose reading 616A. In an incomplete status, the patient bar may displays an icon 616B, such as, for example and without limitation, "- - -," to indicate the incomplete status. Under an incomplete status, the patient's transceiver may be connected but is not currently receiving glucose data or there is a lack of sufficient glucose data to generate a value. An incomplete status may be due to, for example and without limitation: (1) the analyte sensor being in a "Warm-Up Phase," (2) the analyte sensor being in an initialization phase of calibration, or (3) the user has received an alert that prevents glucose data from being displayed. In some embodiments, in an offline status, the patient bar may display the text "Offline" 616C. In some embodiments, if the connection between the transceiver 120 and the primary display device 130 (or between the primary display device 130 and the secondary display device 150), the patient bar may display the text "Transmitter Disconnected" 616D. In a "Transmitter Disconnected" status, there is no connection between the transceiver 120 and the primary display device 130 (or between the primary display device 130 and the secondary display device 150). A "Transmitter Disconnected" status may be due to, for example and without limitation: (1) the battery of the transmitter needing to be recharged, (2) the communication link or the device operated by the patient is off, (3) the transmitter is out of range from the sensor, (4) the transmitter is turned off, or (5) the user has turned off "Auto Sync."

Figures 12D, 12E:
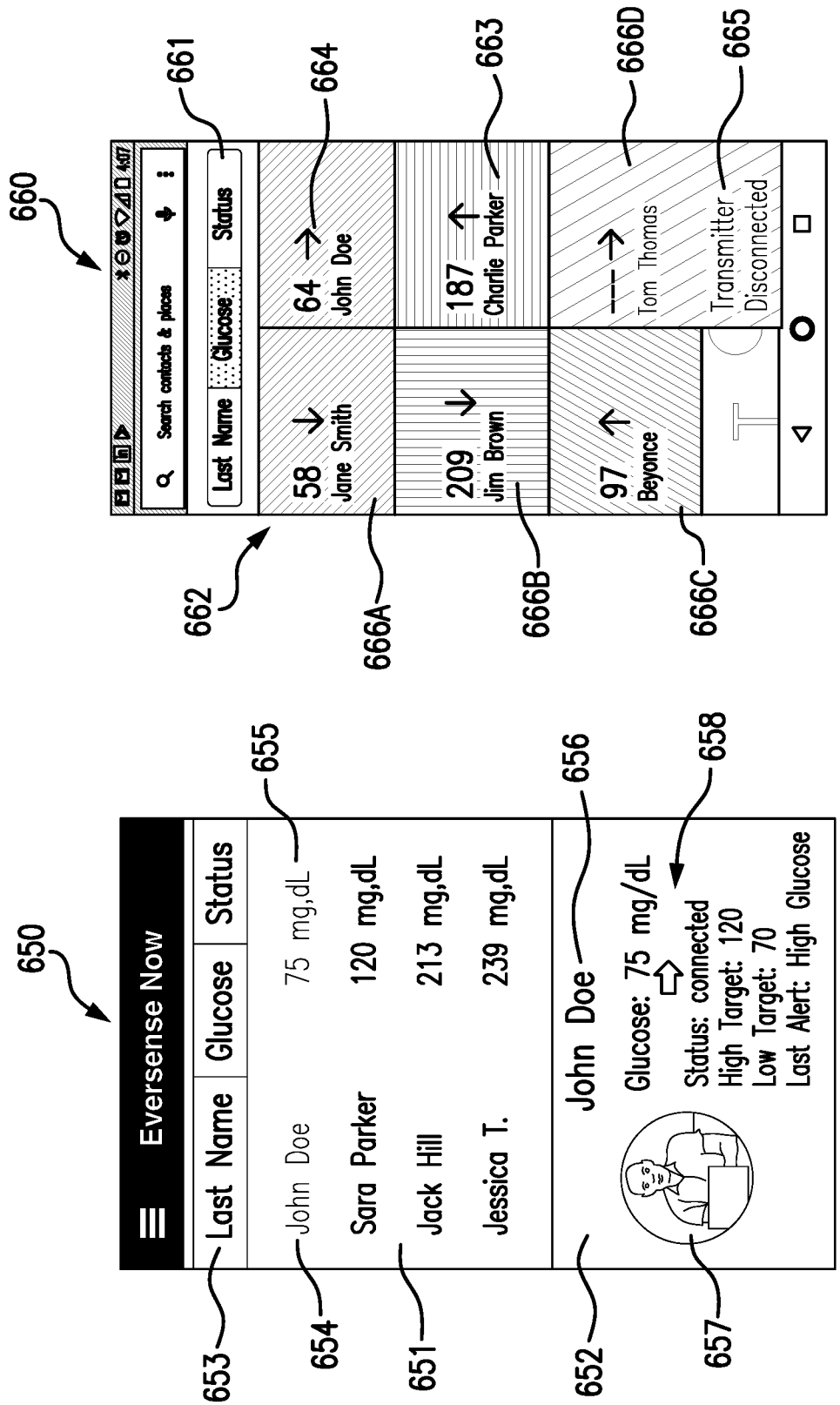

FIG. 12D shows a non-limiting example of a home screen 650 generated by the observer application for display on a GUI of a secondary display device 150 in accordance to various alternative embodiments of the present invention. In some alternative embodiments, as shown in FIG. 12D, the home screen 650 may be bifurcated into two windows: a first window 651 and a second window 652. In some non-limiting embodiments, the first window 651 may be generated in the upper half of the GUI, and the second window 652 may be generated in the lower half of the GUI. In some embodiments, the first window 651 may depict a list of patient accounts whose analyte information is followed by the observer application. In some embodiments, each patient account may be represented by a patient's name 654 and a current analyte measurement 655 of a patient. In some embodiments, the first window 651 may include a navigation bar 653 disposed above the list of patient accounts. The navigation bar 653 may be configured to allow a user to sort the list of patient names 654 by different criteria, such as, for example and without limitation, one or more of alphabetical order as to the last names of the patient, the glucose value of the patients, and the status of the patient. In some embodiments, each patient name 654 depicted in the list of patient accounts of the first window 651 may be configured to be selected by a user to generate a status profile of the selected patient account in the second window 652. In some embodiments, the status profile generated in second window 652 of the home screen 650 may include one or more of a name 656 of the selected patient, a profile picture 657 of the selected patient, and analyte information 658 associated with the selected patient. In some embodiments, the analyte information 658 associated with the selected patient may include one or more of a current analyte measurement, a trend arrow indicating rate and direction of an analyte level change, a status of the patient account, a high target analyte level, a low analyte target level, and a type of the last alert reported by medical application.

FIG. 12E shows a non-limiting example of a home screen 660 generated by the observer application for display on a GUI of a secondary display device 150 in accordance to various alternative embodiments of the present invention. In some alternative embodiments, as shown in FIG. 12E, the home screen 660 may display an array of patient icons 662. In some embodiments, each patient icon 662 in the array may be associated with a respective patient account that is followed by the observer application. In some embodiments, each patient icon 662 may include one or more of a patient's name 663, analyte information 664, and a status 665 of the patient account. The analyte information 664 may include one or more of a current analyte measurement, a trend arrow indicating rate and direction of an analyte level change, and an alert or notice regarding the current analyte measurement. In some embodiments, the home screen 660 may include a navigation bar 661 disposed above the array of patient icons 662. The navigation bar 661 may be configured to allow a user to sort the array of patient icons 662 by different criteria, such as, for example and without limitation, one or more of alphabetical order as to the last names of the patient, the glucose value of the patients, and the status of the patient. In some embodiments, a background color 666A-D of the patient icons 662 may be altered to indicate an alert or status regarding the current analyte level of the respective patient. In some embodiments, a current analyte measurement that falls below a low analyte alarm level or above a high analyte alarm level may be depicted by a first color 666A (e.g., red). In some embodiments, a current analyte measurement that falls between a low alarm analyte level and a low target analyte level or between a high alarm analyte level or a high target analyte level may be depicted by a second color 666B (e.g., yellow). In some embodiments, a current analyte measurement that falls between a high and low target analyte level may be depicted by a third color 666C (e.g., green). In some embodiments, if the connection between the transceiver 120 and the primary display device 130 (or between the primary display device 130 and the secondary display device 150) is terminated, the patient icon 662 may be depicted by a fourth color 666D (e.g., white).

Figure 13:
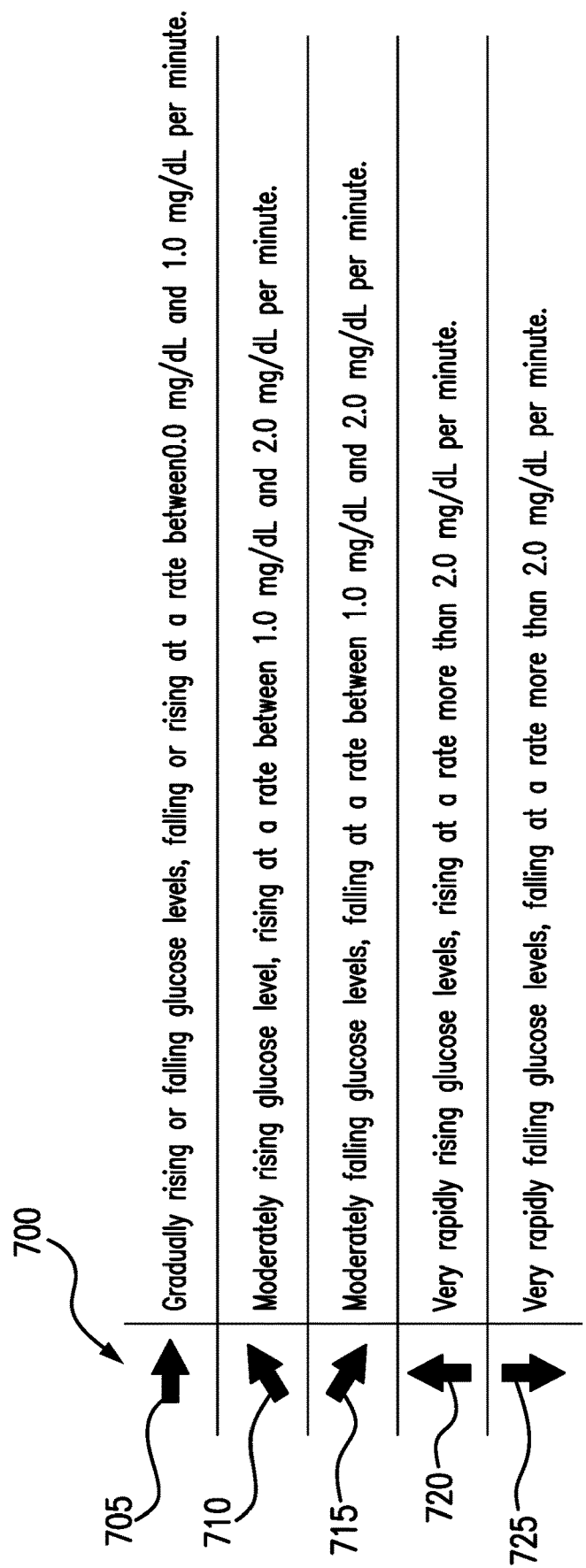
FIG. 13 shows various example trend arrow icons embodying aspects of the present invention.

FIG. 13 shows an example of a trend arrow 700. In some embodiments, the trend arrow 700 may be depicted in five different configurations that signify direction (up, down, neutral) and rate (rapidly, very rapidly slow, slow, very slow, and stable) of analyte change according to an embodiment of the present invention. In some embodiments, the observer application and/or the transceiver 120 may use the last twenty minutes of continuous glucose measurement data received from the sensor and/or processed by the transceiver 120 in the calculation used to determine the orientation of the trend arrow. In some embodiments, there may be times when the trend arrow 700 may not be displayed due to, for example, there being insufficient sensor values available for the trend calculation. In some embodiments, a trend arrow 700 displayed in a horizontal orientation 705 (approximately 0° along the horizontal direction of the GUI display) may indicate that the glucose level is changing gradually, such as, for example, at a rate between −1.0 mg/dL and 1.0 mg/dL per minute. In some embodiments, a trend arrow displayed slightly in the upwards direction 710 (approximately 45° up from the horizontal direction of the GUI 778 display) may indicate that the glucose level is rising moderately, such as, for example, at a rate between 1.0 mg/dL and 2.0 mg/dL per minute. In some embodiments, a trend arrow 700 displayed slightly in the downwards direction 720 (approximately 45° down from the horizontal direction of the GUI display) may indicate that the glucose level is falling moderately, such as, for example, at a rate between 1.0 mg/dL and 2.0 mg/dL per minute. In some embodiments, a trend arrow 700 displayed in a vertical direction 725 (approximately 90° up from the horizontal direction of the GUI 778 display) may indicate that the glucose level is rising very rapidly, such as, for example, at a rate more than 2.0 mg/dL per minute. In some embodiments, a trend arrow 700 displayed in a downwards direction 730 (approximately 90° down from the horizontal direction of the GUI display) may indicate that the glucose level is falling very rapidly, such as, for example, at a rate more than 2.0 mg/dL per minute. In some embodiments, the trend arrow 700 is different from a predicted glucose alarm or alert. For example, the trend arrow may indicate rate and direction of change regardless of glucose value, whereas predicted glucose alarms or alerts may indicate reaching a certain glucose level based on current trends. For example, the application may cause a predicted low glucose alarm or alert to be displayed in the notification bar while still displaying a relatively stable trend arrow (e.g., at 0° or 45° from the horizontal direction of the GUI display).

Trend Graph Screen

Figure 14A:
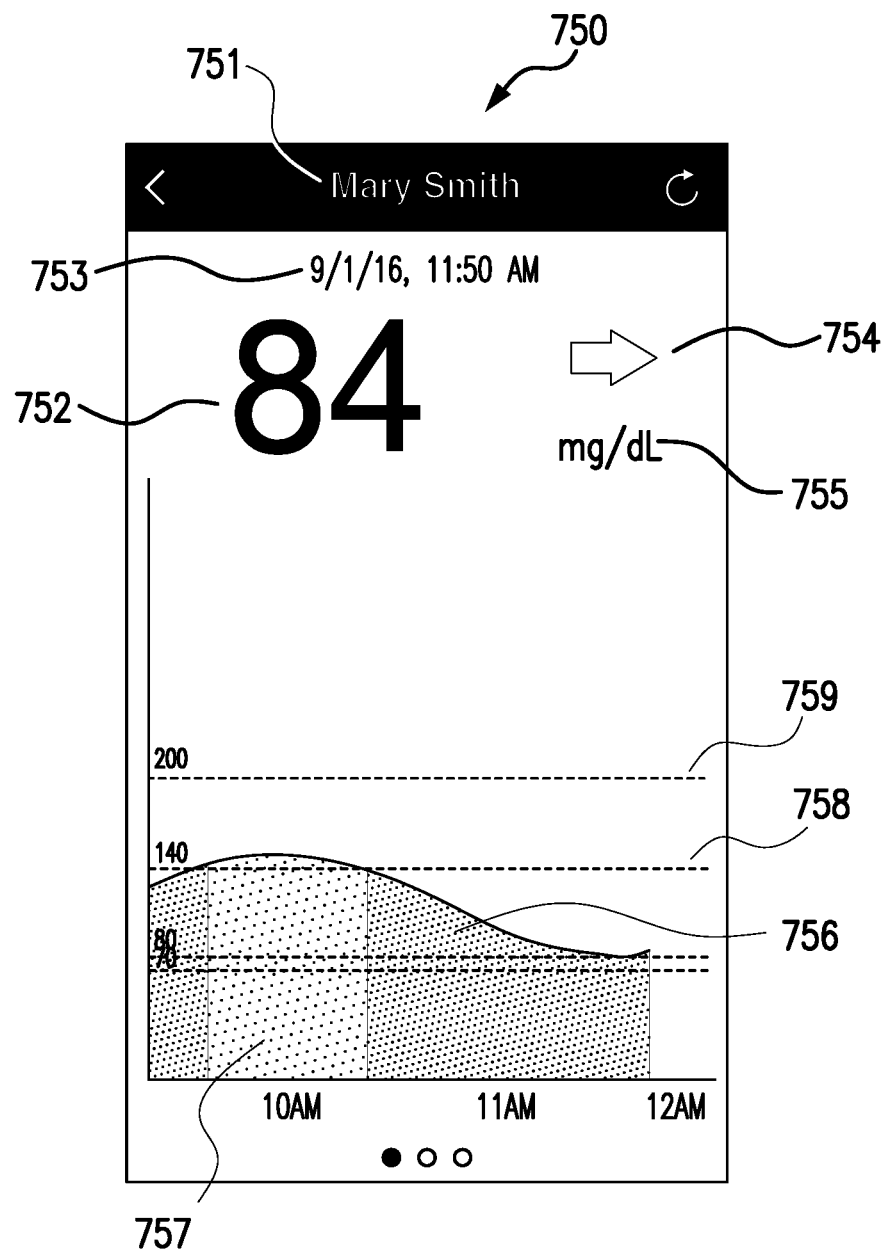
FIGS. 14A and 14B show various example trend graph screens embodying aspects of the present invention.

FIG. 14A shows an example of a trend graph screen 750 generated by the observer application for display on a GUI of a secondary display device 150 in accordance to an embodiment of the present invention. In some embodiments, to gain access to the trend graph screen 750 of a particular patient's account, a user may select the patient bar on the home screen. For example, if the display on a device is a touchscreen, the user may simply tap the patient bar on the home screen to generate the trend graph screen of that particular patient's account. As shown in FIG. 14A, the trend graph screen 750 may present one or more of the name of the patient 751, a numerical value 752 of the current glucose reading, the date and time 753 of the current glucose reading, a trend arrow 754 indicating rate and direction of analyte or glucose level change, the unit of measure 755, and graphical trends, such as a historical line graph 756, of analyte or glucose levels over a select period of time. As shown in FIG. 14A, in some embodiments, the historical line graph 756 may include a set of lines 758 indicating a target range selected by a user, a set of lines 759 indicating high and low alert levels 759 selected by a user, and portions 757 under the trend line of the graph 756 that indicate whether analyte measurements from a patient fall within or out of the target or alert levels. However, the trend graph screen 750 may disclose other types of information items in different embodiments. For example, Table 1 below depicts several informational non-limiting examples of items and features that may be depicted on the trend graph screen.

TABLE 1

Trend Graph Screen

| | |
|---|---|
| Status bar | Shows the status of user's glucose level |
| Transceiver/Transmitter ID | This is the transceiver being used; the transceiver name can be changed by going to Settings > System |
| Current glucose value | A real-time glucose reading; this may be updated every 5 minutes |
| Date and time | The current date and time with navigational options, such as scroll left or right to see different dates and times |
| Alarm and Events | Shows an icon when an alert, alarm, or event occurs |
| Bluetooth Connection | Shows the strength of the Bluetooth connection |
| Handheld Device Battery Level | Indicates the battery strength of the handheld device |
| Transmitter/Transceiver Battery Level | Indicates the battery strength of the transceiver |
| Transmitter/Transceiver Connection Status Icon | Shows the strength of the transceiver connection |
| Trend Arrow | Shows the direction a patient's glucose level is trending |
| Unit of Measurement | This is the units for the glucose value |
| High Glucose Alarm Level | This is the high glucose alarm or alert level set by a user |
| Glucose High Target Level | This is the high glucose target level set by a user |
| Stacked Alerts | Shows when there are several alerts at the same time |
| Glucose Trend Graph | A user can navigate or scroll through the graph to see the trend over time |
| Calibration Point Icon | This icon appears when a calibration is entered |
| Profile Indicator | This indicator may indicate what profile is being applied, such as a normal profile, temporary profile, vacation profile, and the like. |

In some embodiments, the graphical trend may be depicted by a historical graph of glucose levels over a select period of time. The historical graph may depict logged events and/or user inputted activities such as meals (nutrition, amount of carbohydrates), exercise (amount of exercise), medication (amount of insulin units), and blood glucose values as icons on positions of the graph corresponding to when such events occurred. The historical graph may further show one or more of a boundary or indication of a high glucose alarm level, a low glucose alarm level, a high glucose target level, and a low glucose target level, described in further detail below. In some embodiments, a user may interact with a time or date range option via GUI to adjust the time period of the glucose level displayed on the historical graph. The date range may be specified by a user and may bet set to different time periods such as 1, 3, 24 hours, 1, 7, 14, 30, and 60 days, weeks, months, etc. In some embodiments, the line graph may show high, low, and average glucose levels of a patient for the selected date range. In other embodiments, the line graph may be a pie chart, log book, modal day, or other depiction of glucose levels of a patient over a selectable date range, any of which may further depict high, low, and average glucose levels of the patient over that date range.

Figure 14B:
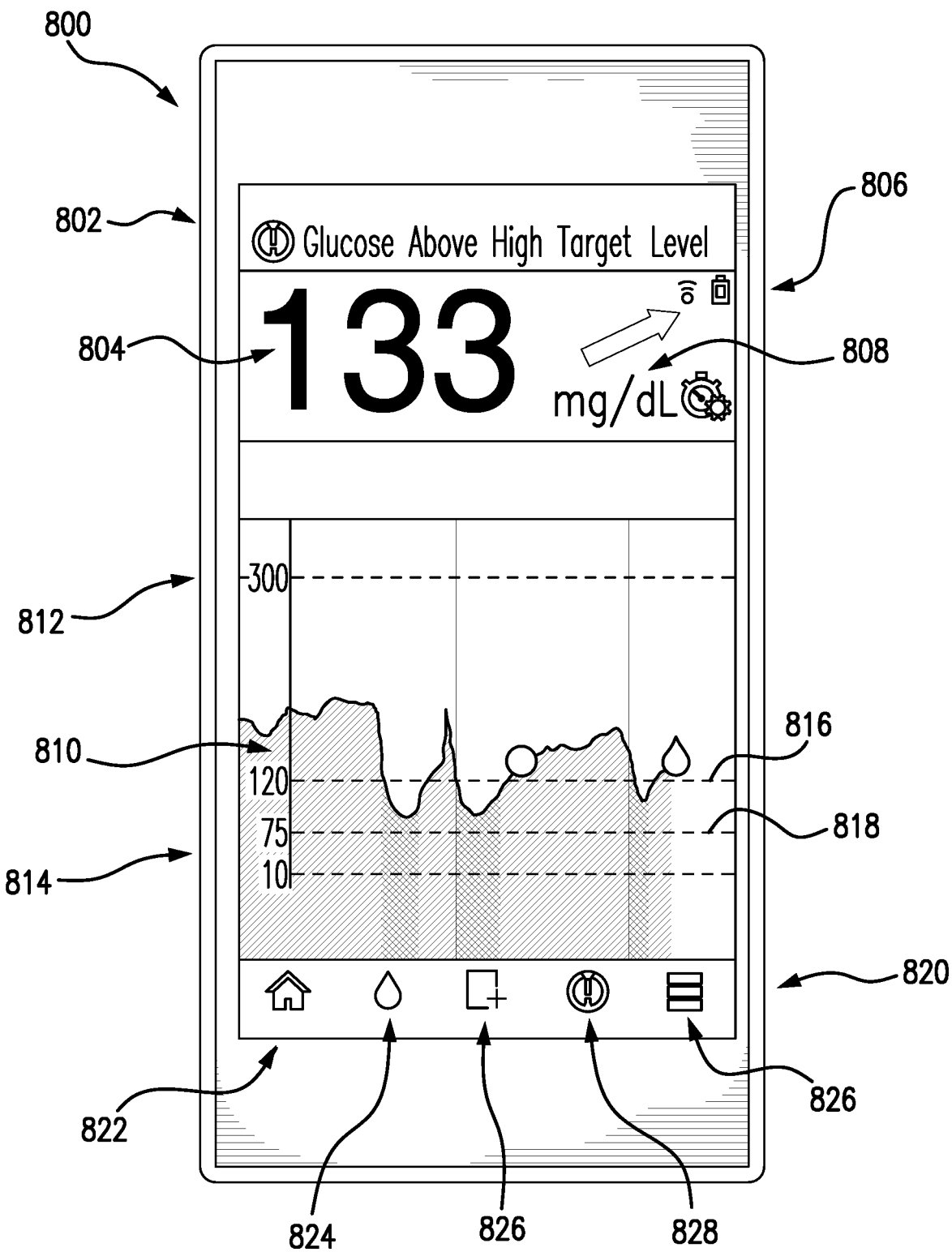

FIG. 14B shows a trend graph screen 800 generated by the observer application for display on a GUI of a device in accordance to another embodiment of the present invention. As shown in FIG. 14B, in some embodiments, the trend graph screen 800 may comprise one or more of: a status notification bar 802 that may depict, for example, alarms, alerts, and notifications related to, for example, glucose levels and system statistics and/or status; a real-time current glucose level 804 of a patient; one or more icons representing sensor or transmitter/transceiver signal strength and transmitter/transceiver battery level 806; a trend arrow 808 reflecting a rate and/or direction of change in glucose measurements of a patient; a historical graph, such a line graph 810 with alarm levels 812, 814 and target levels 816, 818, reflecting trends of glucose measurement levels of a patient; a profile indicator; and navigation tools 820 that allow a user to navigate through different areas or screens that may be generated in the GUI by the application, such as "Home" 822, "Calibrate" 824, "Event Log" 826, "Notifications" 828, and "Menu" 828 screens.

In some embodiments, the observer application may cause the device to provide auditory readings of the information items depicted on the trend graph screen, for example, to allow users who are visually impaired and/or illiterate to use the application and device. For example, the observer application may cause the device provide an auditory reading via an audio interface of the current glucose level, trend arrow, any alerts or alarms displayed in status notification bar, as well as other information items on the trend graph screen of the observer application.

In some embodiments, the historical line graph may allow user to quickly review and analyze historical data and/or trend information of a patient's sensor glucose measurement values over time. In some embodiments, the historical line graph may include icons or markers along the trend line to reflect alarms, alerts, notifications, and/or any events that were automatically or manually logged by the patient. Where one or more of such icons or markers are displayed on the historical line graph, a user may select any one of the icons or markers to obtain more information about the item. For example, in response to a selection of a mark on the line graph, the GUI may generate a popup window on the display that provides more information about the mark.

In some embodiments, the historical line graph may enable a user to quickly review how well a patient is doing against glucose targets and/or alarms or alerts. For example, as described in further detail below, a user may establish a high glucose alarm level and/or a low glucose alarm level, as well as a high glucose target level and/or a low glucose target level. The high glucose alarm level and/or low glucose alarm level may be visually depicted over the historical line graph, for example, using a colored dashed line (such as red). Additionally, the high glucose target level and low glucose target level may be visually depicted over the historical line graph, for example, using a color dashed line (such as green).

In some embodiments, the colors of the historical line graph may change depending on a glucose level status. For example, during the times where the glucose level was outside of the high glucose alarm level or low glucose alarm level, then the portion of the line graph corresponding to those times may be filled in red. As another example, during the times where the glucose level is between the high glucose target level and the low glucose target level, then the portion of the line graph corresponding to those times may be filled in green. As yet another example, during the times where the glucose level is between a glucose target level and a corresponding alarm level, then the portion of the line graph may be filled in yellow.

In some embodiments, the line graph may be displayed with one or more selectable date range icons that allow a user to change the day/time period corresponding to the line graph in real-time. For example, a user may select a forwards or backwards selectable option (such as an arrow) or use a swipe or fling gesture that may be recognized by GUI to navigate to a later or earlier time period, respectively, such as a day, month, etc. In some embodiments a user may choose an older graph to display by tapping the date on the date range portion of the screen and submitting or entering a desired date and/or time to review. In some embodiments, a user may use one or more gestures that are recognized by the GUI, such as a pinch, zoom, tap, press and hold, or swipe, on graph. For example, a user may pinch the historical line graph with a thumb and index finger in order to cause the observer application to display different time/dating settings or adjust a time/date setting on the line graph. In some embodiments, a user may tap or press and hold a time event on historical line graph, and in response the application may display further detail on the time event, such as a history, reading value, date/time, or association to other events or display a prompt for entry of a time event.

In some embodiments, the observer application may store glucose data on the analyte monitoring device so long as there is available memory space. Additionally or alternatively, the observer application may cause the device to send a sync request message to store the glucose data on a remote storage device.

Alerts and Notifications

In some embodiments, one or more of the patient application and the observer application may be configured to generate alarms, alerts, and/or notifications as a display on the GUI. In one embodiment, when the patient application generates an alarm, alert, and/or notification as a display on a primary display device 130, the observer application will generate an alarm, alert, and/or notification as a display on a secondary display device 150. Accordingly, the primary display device 130 and the secondary display device 150 linked together over the network of the analyte monitoring system may both receive an alarm, alert, and/or notification at approximately the same time, thereby allowing a patient and the identified group of followers to receive important analyte information approximately simultaneously.

Figure 15:
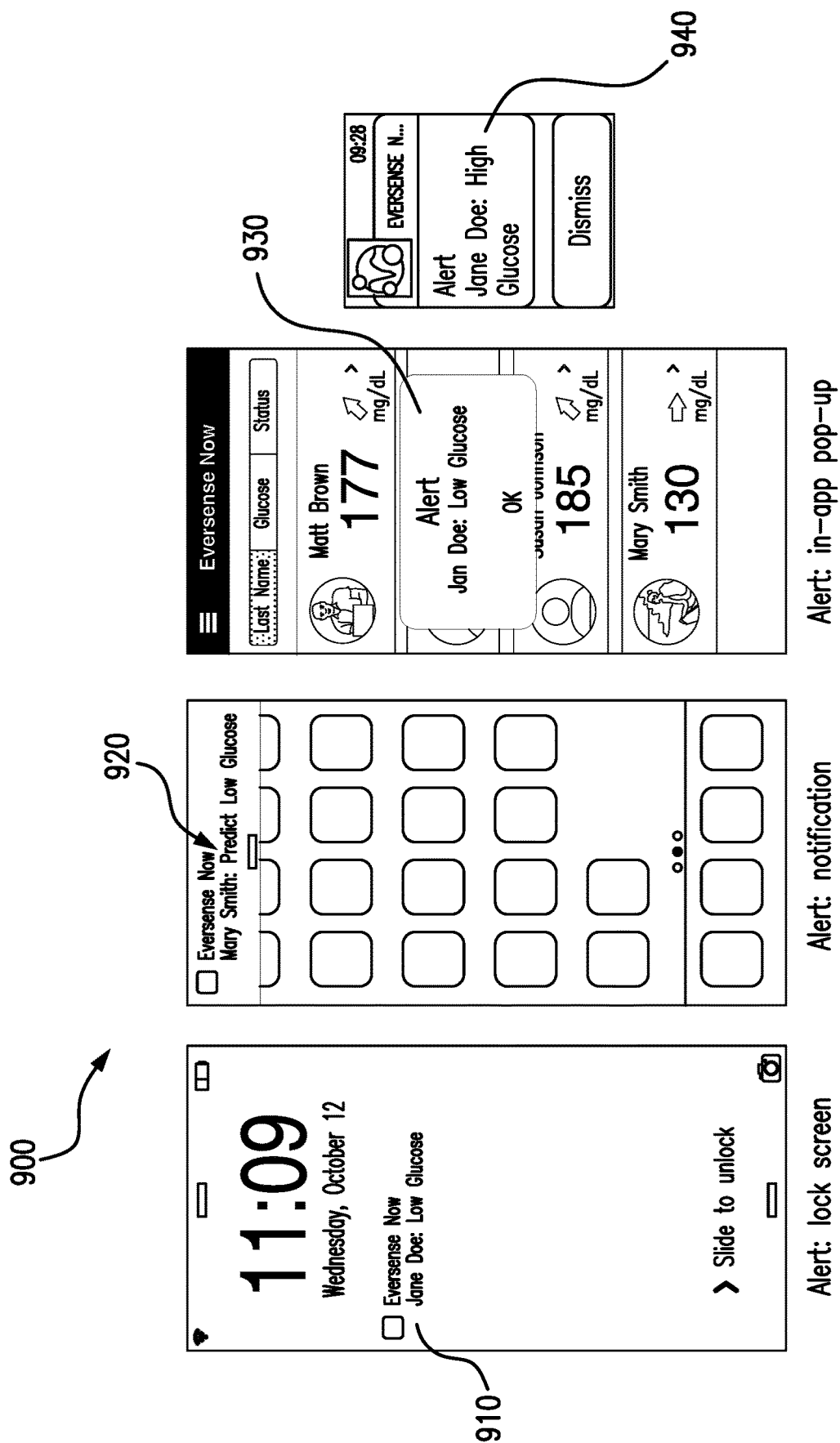
FIG. 15 shows various example notification screens embodying aspects of the present invention.

FIG. 15 shows examples of notifications 900 that may be generated by the observer application for display on a GUI of a secondary display device 150 in accordance to an embodiment of the present invention. In some embodiments, the observer application may configure the secondary display device 150 to generate an alarm, alert, and/or notification as an icon 910 on the lock screen of the secondary display device 150. In some embodiments, the observer application may configure the secondary display device 150 to generate an alarm, alert, and/or notification as a status bar 920 depicted at the top of the screen of the secondary display device 150. In some embodiments, the observer application may configure the secondary display device 150 to generate an alarm, alert, and/or notification as a pop-up icon 930 displayed in the center of the screen of the secondary display device 150. In some embodiments, the observer application may configure the secondary display device 150 to generate an alarm, alert, and/or notification as a display 940 on a mobile watch. In other embodiments, the observer application may configure the secondary display device 150 to generate alarms, alerts, and notifications in the form of vibrations, sounds, or other visual alarms. For example, the observer application may configure the secondary display device 150 to generate fast vibrations for high glucose and/or slower vibrations for low glucose may be used. The higher or lower frequency can be either vibration frequency or vibration pulses.

In some embodiments, the observer application may provider follower adjustable notifications that allow a user of the observer application executing on a secondary display device 150 to indicate if received CGM data and/or notifications from the patient application executing on the primary display device 130 are too high/low and/or out of scope. In some embodiments, the observer application may also allow the user to view the last five alerts/alarms/notifications of a followed application account/patient and/or the last five BGM measurements taken by the followed application account/patient. In some embodiments, the observer application may export the shared CGM data and/or notifications information from the secondary display device 150 to be displayed on a personal computer, laptop, or other computing device.

Alert History Screen

Figure 16:
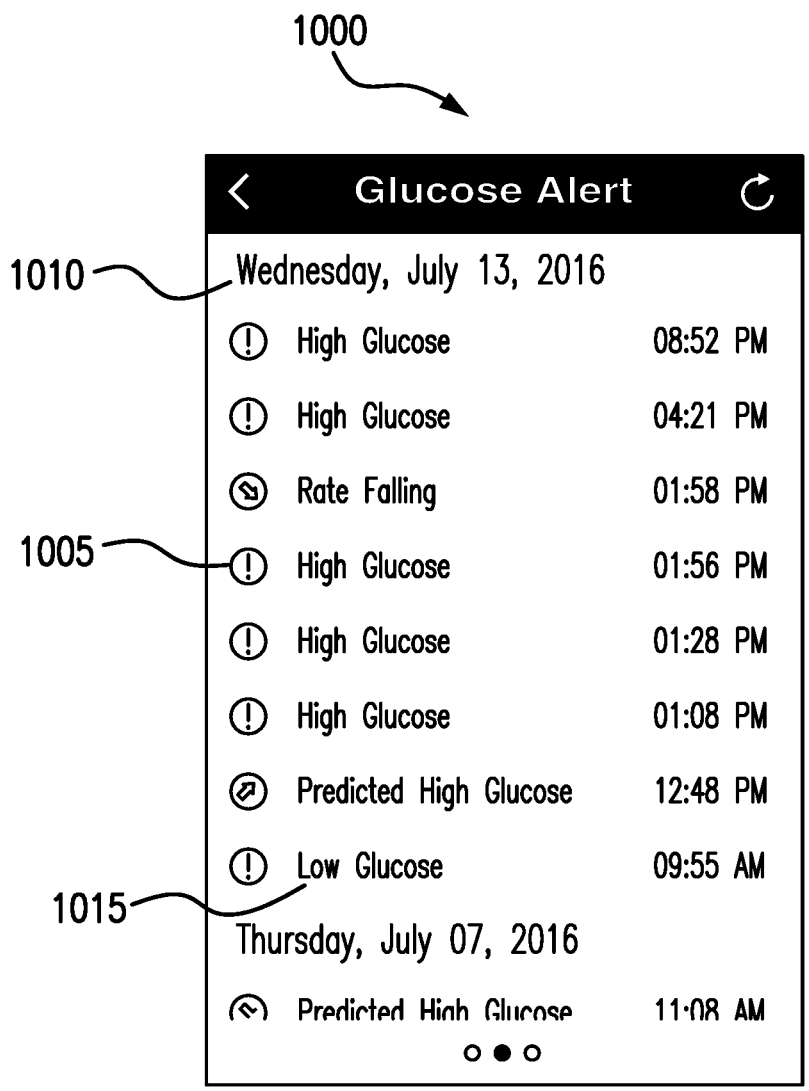
FIG. 16 shows an example alert history screen embodying aspects of the present invention.

FIG. 16 shows an example of an alert history screen 1000 that may be generated by the observer application for display on a GUI of a secondary display device 150 in accordance to an embodiment of the present invention. In one embodiment, a user may gain access to the alert history screen 1000 of a particular patient's account by swiping the trend graph screen of the patient's account to the left. As shown in FIG. 16, the alert history screen 1000 may present a list of alarms, alerts, and notifications 1005 that may be generated by the observer application over time, thereby enabling a user to review past messages that may have been missed or to help a user understand more about the glucose status of a patient. In some embodiments, all alarms, alerts, and notifications for a specific date 1200, such as today's date, may be display in list. The alarms, alerts, and notifications may relate to events such as the rising or falling of glucose rates as well as low or high glucose values (i.e. hypoglycemia or hyperglycemia).

In some embodiments, each alarm, alert, or notification in list may be accompanied by one or more information items, such as, for example and without limitation, a brief textual description 1205, a time and/or date, and an icon that may indicate the type, severity, and/or frequency of the notification, alarm, or alert. In some embodiments, each notification, alert, and/or alarm in the list may be selectable in the GUI, and upon selection of a notification, alert, and/or alarm, the application may cause a screen to appear indicating additional details of the alarm, notification, and/or alert, such as the time, actions to take, recommendations, etc. Where the notifications, alerts, and/or alarms in the list span beyond the display area of the analyte monitoring device, the application may configure the GUI to allow a user to navigate through the list using a gesture, such as a scroll or flick, recognized by GUI and/or provide a selectable date option to allow a user to jump to a different date of notifications, alarms, and/or alerts.

In some embodiments, each notification, alarm, and/or alert may correspond to a different type, severity, and/or frequency, which may be represented as a specific icon. For example, icon may indicate a critical alarm, icon may indicate a non-critical alert, icon may indicate a non-critical notification, icon may indicate more than one alarm in the same period, and icon may indicate a battery alarm for the transceiver. In some embodiments, different icons may be used to indicate the same or different types, frequency, and/or severity of alarms, alerts, and notifications as shown in the legend.

Event Log Screen

Figure 17A:
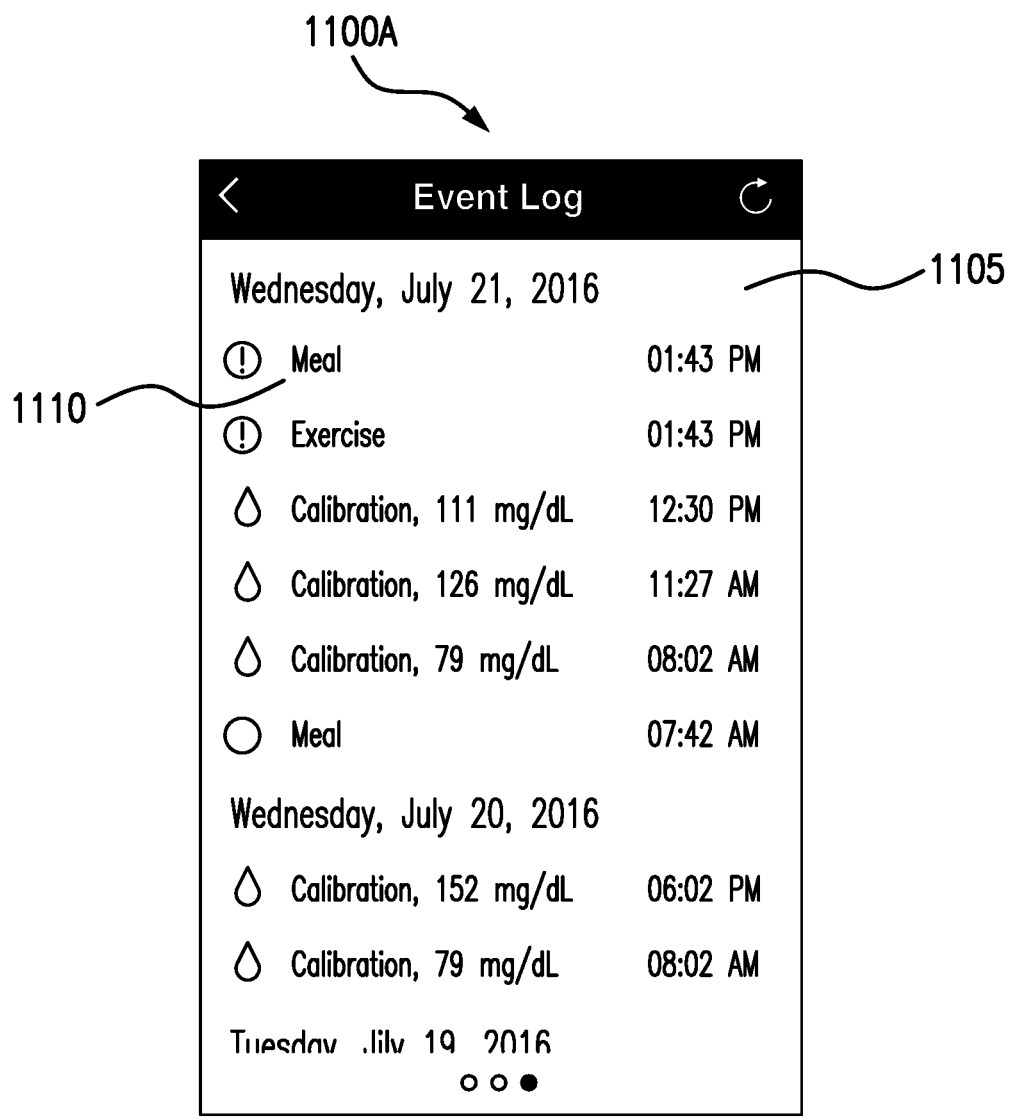
FIGS. 17A and 17B show various example event log screens embodying aspects of the present invention.

FIG. 17A shows an example of an event log screen 1100A that may be generated by the observer application for display on a GUI of a device according to an embodiment of the present invention. In some embodiments, a user may gain access to the event log screen 1100A of a particular patient's account by swiping the alert history screen of the patient's account to the left. As shown in FIG. 17A, in some embodiments, the event log screen 1100A may present an event log 1105 with one or more past events 1110. The event log may list all or a subset of events entered by a user over a specific time period (e.g., a day, a week, a month, a year, etc.). Where the events in the event log span beyond the display area of the device, the observer application may configure the GUI to allow a user to use a gesture, such as a scroll or flick, that is recognized by the GUI to navigate through the event entries or configure the GUI to provide a selectable date option to allow a user to navigate to a different date of events. In some embodiments, each event in the event log may be selectable in the GUI, and upon selection of the event a screen may appear indicating one or more additional details of the event, such as the time, notes, values, measurements, etc. associated with the event.

Figure 17B:
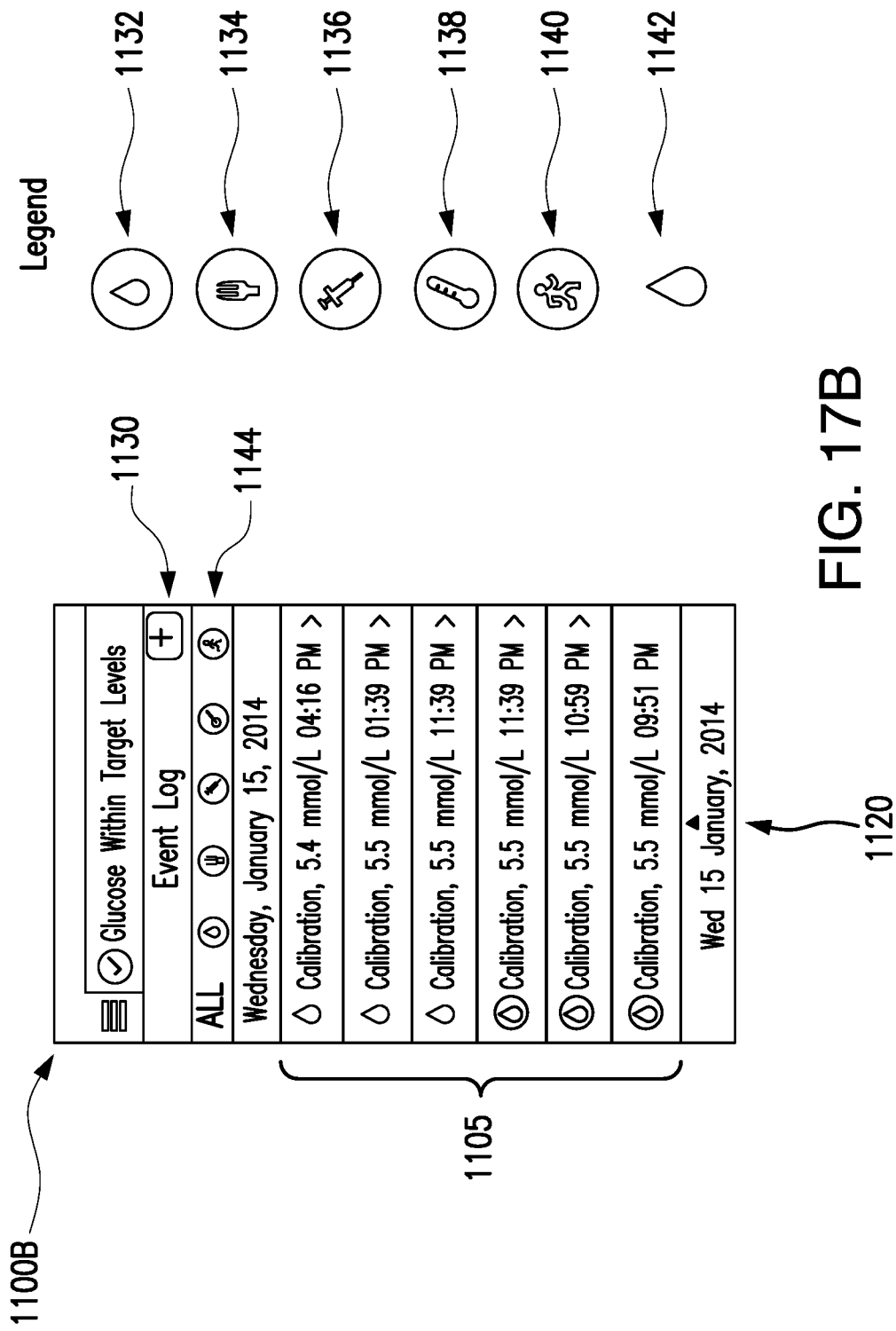

FIG. 17B shows an example of an event screen 1100B generated by the observer application for display on a GUI of a secondary display device 150 in accordance with another embodiment of the present invention. As shown in FIG. 17B, the event screen 1100B may depict an event log 1105 with one or more past events. The event log 1105 may list all or a subset of events entered by a user over a specific time period (e.g., a day, a week, a month, a year, etc.). Where the events in the event log 1105 span beyond the display area of the device, the observer application may configure the GUI to allow a user to use a gesture, such as a scroll or flick, that is recognized by the GUI to navigate through the event entries or configure the GUI to provide a selectable date option 1120 to allow a user 715 to navigate to a different date of events. In some embodiments, each event in the event log 1105 may be selectable in the GUI, and upon selection of the event a screen may appear indicating one or more additional details of the event, such as the time, notes, values, measurements, etc. associated with the event. In some embodiments, a user may manually add event entries by selecting an add event option 1130.

Each event may correspond to an event type, which may be represented in short-hand with a symbol and/or a specific icon such as those shown in FIG. 17B. For example, icon may indicate a BGM test event 1132, icon may indicate a meal event 1134, icon may indicate an insulin dosage event 1136, icon may indicate a health condition event 1138, icon may indicate an exercise event 1140, and icon may indicate a calibration measurement 1142. In some embodiments, different icons may be used to indicate the same or different events as those shown in the legend.

Where the observer application specifies event types, such as those shown in the legend in FIG. 17B, the event screen may display a set of one or more selectable filtering options 1144 to filter the types of events displayed in the event log. When the "all" events option is selected by a user, all events regardless of type may be displayed in the event log. However, upon the selection of a selectable event filtering option by a user, which may be represented as one or more icons, such as those shown in the legend, only events corresponding to the selected filtering option may be displayed. For example, if a user selects the icon corresponding to BGM tests, then the observer application may only display events, if any, that reflect BGM tests in the event log.

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. For example, in some alternative embodiments, one or more of the primary and secondary display devices may be a medical device such as, for example and without limitation, a blood glucose meter, an insulin pump, or a combination thereof. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. An analyte monitoring system comprising:
    an analyte sensor including:
        an indicator element that exhibits one or more detectable properties based on an amount or concentration of glucose in interstitial fluid in proximity to the indicator element, and
        a transceiver interface device configured to convey sensor data including one or more measurements of the one or more detectable properties;
    a transceiver configured to:
        receive the sensor data conveyed from the analyte sensor,
        calculate analyte information using at least the received sensor data, wherein the analyte information includes at least a glucose concentration, and
        convey the analyte information;
    a primary display device configured to:
        receive the analyte information conveyed from the transceiver,
        display the received analyte information, and
        convey the analyte information over a network;
    a remote computing device configured to receive and store the analyte information conveyed from the primary display device over the network; and
    a secondary display device configured to:
        receive the analyte information from the remote computing device over the network, and
        display the received analyte information.

2. The analyte monitoring system of claim 1, wherein the remote computing device comprises a server.

3. The analyte monitoring system of claim 1, wherein the analyte sensor is a first analyte sensor, the indicator element is a first indicator element, the sensor data is first sensor data, the transceiver is a first transceiver, the analyte information is first analyte information, and the primary display device is a first primary display device, and the analyte monitoring system further comprises:
    a second analyte sensor including:
        a second indicator element that exhibits one or more detectable properties based on an amount or concentration of glucose in interstitial fluid in proximity to the second indicator element, and
        a second transceiver interface device configured to convey second sensor data including one or more measurements of the one or more detectable properties;
    a second transceiver configured to:
        receive the second sensor data conveyed from the second analyte sensor,
        calculate second analyte information using at least the received second sensor data, wherein the second analyte information includes at least a glucose concentration, and
        convey the second analyte information; and
    a second primary display device configured to:
        receive the second analyte information conveyed from the second transceiver,
        display the received second analyte information, and
        convey the second analyte information over the network;
    wherein the remote computing device is further configured to receive the second analyte information conveyed from the second primary display device over the network, and the secondary display device is further configured to:
        receive the second analyte information from the remote computing device over the network, and
        display the received second analyte information.

4. The analyte monitoring system of claim 1, wherein the primary display device comprises a storage medium and a processor, the storage medium stores a patient application in the form of computer readable instructions, the processor is configured to execute one or more of the computer readable instructions of the patient application, and the patient application is configured to allow a user of the primary display device to share analyte information with the secondary display device.

5. The analyte monitoring system of claim 1, wherein the secondary display device comprises a storage medium and a processor, the storage medium stores an observer application in the form of computer readable instructions, the processor is configured to execute one or more of the computer readable instructions of the observer application, and the observer application is configured to allow a user of the secondary display device to receive and view analyte information from the primary display device.

6. A method comprising:
    measuring, by an analyte sensor, one or more detectable properties that are exhibited by an indicator element based on an amount or concentration of glucose in interstitial fluid in proximity to the indicator element;
    conveying, by a transceiver interface device of the analyte sensor, sensor data including one or more measurements of the one or more detectable properties;
    receiving, by a transceiver, the sensor data conveyed by the analyte sensor;

calculating, by the transceiver, analyte information using at least the received sensor data, wherein the analyte information includes at least a glucose concentration;

conveying, by the transceiver, the analyte information;

receiving, by a primary display device, the analyte information conveyed by the transceiver;

conveying, by the primary display device, the analyte information over a network;

receiving, by a remote computing device, the analyte information over the network;

storing, by the remote computing device, the analyte information; and transmitting, by the primary display device, an invitation authorizing access to the analyte information stored in the remote computing device over a network to one or more secondary display devices, wherein each secondary display device is configured to be used by a respective user who is remote to the analyte sensor.

7. The method of claim 6, wherein the analyte information comprises one or more of: (i) an alert, (ii) an alarm, and (iii) glucose concentration trend information.

8. The method of claim 6, wherein the analyte information comprises one or more of a high analyte alarm level, a low analyte alarm level, a high target analyte level, and a low target analyte level.

9. The method of claim 6, wherein the transceiver comprises a sensor interface device configured to convey a power signal to the analyte sensor and to receive data signals conveyed by the analyte sensor.

10. A method comprising:

receiving, at a secondary display device, an invitation transmitted from a primary display device, wherein the invitation authorizes the secondary display device to access analyte information, and the secondary display device is remote from the primary display device;

receiving, by the secondary display device, the analyte information, wherein the analyte information comprises a glucose concentration and one or more of: (i) an alert, (ii) an alarm, and (iii) glucose concentration trend information;

generating, by the secondary display device, one or more alarms, alerts, or notifications based on the received analyte information;

displaying, by the secondary display device, a plurality of host status bars, wherein one of the plurality of the host status bars identifies a host associated with the primary display device and indicates a status of the host using at least a portion of the received analyte information;

receiving, via a user input to the secondary display device, a selection of one of the plurality of the host status bars; and displaying, by the secondary device, an analyte trend graph associated with the selected one of the plurality of the host status bar, wherein the analyte trend graph comprises a trend line indicating a plurality of analyte concentrations over a first time interval;

wherein the analyte information comprises one or more of: (i) an analyte concentration (ii) an alert, (iii) an alarm, and (iv) analyte concentration trend information.

11. The method of claim 10, wherein the analyte information comprises an analyte concentration and one or more of: (i) an alert, (ii) an alarm, and (iii) analyte concentration trend information, and the trend line indicates a plurality of glucose concentrations over the first time interval.

12. The method of claim 10, comprising:

selecting, by user input to the secondary display device, the displayed analyte trend graph that is associated with the selected host status bar; and displaying, by the secondary display device, a list of alarms, alerts, and/or notifications over a period of time and a selectable icon corresponding to each alarm, alert, or notification;

wherein each selectable icon indicates one more of a type, a severity, and a frequency of the respective alarm, alert, or notification.

13. The method of claim 12, comprising:

selecting, by user input to the secondary display device, the list of alarms, alerts, and/or notifications associated with a selected one of a plurality of hosts; and displaying, by the secondary display device, an event log depicting a plurality of events associated with the selected host and a selectable icon corresponding to each of the events;

wherein the selectable icon corresponding to each of the plurality of events comprises one or more of: a blood glucose meter test icon, a meal event icon, an insulin dosage icon, a health condition icon, and an exercise event icon.

14. The method of claim 10, further comprising:

determining, by the secondary display device, that the number of the plurality of the host status bars displayed on the secondary display device is equal to a maximum number of hosts; and displaying, by the secondary display device, a message indicating that a number of accepted invitations has met the maximum number of hosts.

15. An analyte monitoring system comprising:

an analyte sensor including an indicator element that exhibits one or more detectable properties based on an amount or concentration of glucose in interstitial fluid in proximity to the indicator element, wherein the analyte sensor is configured to convey sensor data including one or more measurements of the one or more detectable properties;

a primary display device configured to:
receive the sensor data conveyed from the analyte sensor,
calculate analyte information using at least the received sensor data, wherein the analyte information includes at least a glucose concentration,
display the calculated analyte information, and
convey the analyte information over a network;

a remote computing device configured to receive and store the analyte information conveyed from the primary display device over the network; and a secondary display device configured to:
receive the analyte information from the remote computing device over the network, and
display the received analyte information.

16. A method comprising:

measuring, by an analyte sensor, one or more detectable properties that are exhibited by an indicator element based on an amount or concentration of glucose in interstitial fluid in proximity to the indicator element;

conveying, by the analyte sensor, sensor data including one or more measurements of the one or more detectable properties;

receiving, by a primary display device, the sensor data conveyed by the analyte sensor;

calculating, by the primary display device, analyte information using at least the received sensor data, wherein the analyte information includes at least a glucose concentration;

conveying, by the primary display device, the analyte information over a network receiving, by a remote computing device, the analyte information conveyed by the primary display device over the network;

storing, by the remote computing device, the analyte information; and transmitting, by the primary display device, an invitation authorizing access to the analyte information stored in the remote computing device over a network to one or more secondary display devices, wherein each secondary display device is configured to be used by a respective user who is remote to the analyte sensor.

* * * * *